United States Patent
Rao et al.

(10) Patent No.: US 11,998,330 B2
(45) Date of Patent: Jun. 4, 2024

(54) INTERFERENCE REJECTION MEMBRANES USEFUL WITH ANALYTE SENSORS

(71) Applicant: Medtronic MiniMed, Inc., Northridge, CA (US)

(72) Inventors: Ashwin K. Rao, West Hills, CA (US); Qingling Yang, Northridge, CA (US); Ellis Garai, Studio City, CA (US); Daniel E. Pesantez, Canoga Park, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 313 days.

(21) Appl. No.: 17/162,885

(22) Filed: Jan. 29, 2021

(65) Prior Publication Data
US 2022/0240823 A1    Aug. 4, 2022

(51) Int. Cl.
*A61B 5/1486* (2006.01)
*A61B 5/145* (2006.01)
*A61B 5/00* (2006.01)

(52) U.S. Cl.
CPC ...... *A61B 5/14865* (2013.01); *A61B 5/14532* (2013.01); *A61B 5/7246* (2013.01); *A61B 2562/125* (2013.01)

(58) Field of Classification Search
CPC ............ A61B 5/14865; A61B 5/14532; A61B 5/7246; A61B 2562/125
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |

(Continued)

FOREIGN PATENT DOCUMENTS

| | | |
|---|---|---|
| WO | 02097415 A2 | 12/2002 |
| WO | 2015073758 A1 | 5/2015 |
| WO | 2019222499 A1 | 11/2019 |

OTHER PUBLICATIONS

PCT International Search Report and Written Opinion dated May 12, 2022 for PCT Application No. PCT/US2022/014023.

*Primary Examiner* — Alex M Valvis
*Assistant Examiner* — Grace L Rozanski
(74) *Attorney, Agent, or Firm* — GATES & COOPER LLP

(57) ABSTRACT

Embodiments of the invention provide amperometric analyte sensors having optimized elements such as interference rejection membranes, and associated architectures, as well as methods for making and using such sensors. While embodiments of the innovation can be used in a variety of contexts, typical embodiments of the invention include glucose sensors used in the management of diabetes.

10 Claims, 17 Drawing Sheets

(56) References Cited

U.S. PATENT DOCUMENTS

| | | |
|---|---|---|
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2006/0228767 A1* | 10/2006 | Shull .................. C12Q 1/34 435/18 |
| 2007/0123819 A1 | 5/2007 | Mernoe et al. |
| 2009/0101498 A1 | 4/2009 | Papadimitrakopoulos et al. |
| 2010/0160861 A1 | 6/2010 | Causey, III et al. |
| 2014/0286875 A1 | 9/2014 | Gamsey et al. |
| 2015/0079506 A1* | 3/2015 | Kandanarachchi ... C08F 210/10 526/272 |
| 2017/0315077 A1 | 11/2017 | Rao et al. |
| 2018/0047650 A1* | 2/2018 | Barber ............... H01L 23/3157 |
| 2020/0171534 A1* | 6/2020 | Margel ................. B05D 3/108 |

\* cited by examiner

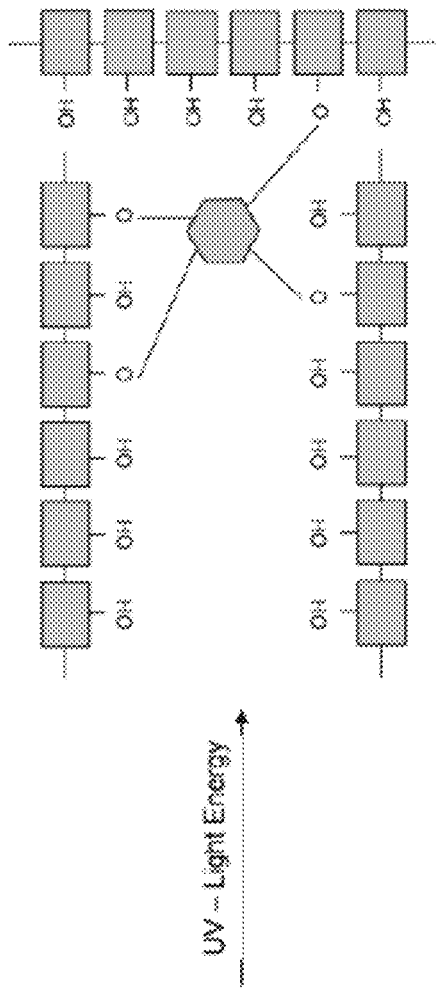
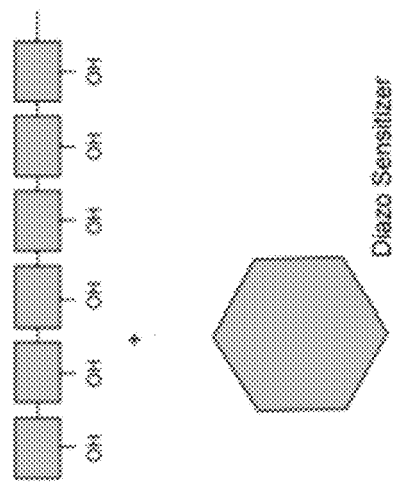
FIGURE 1B

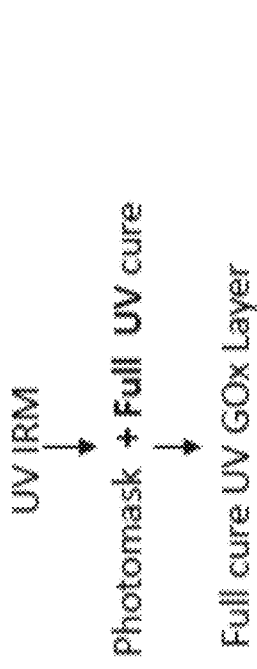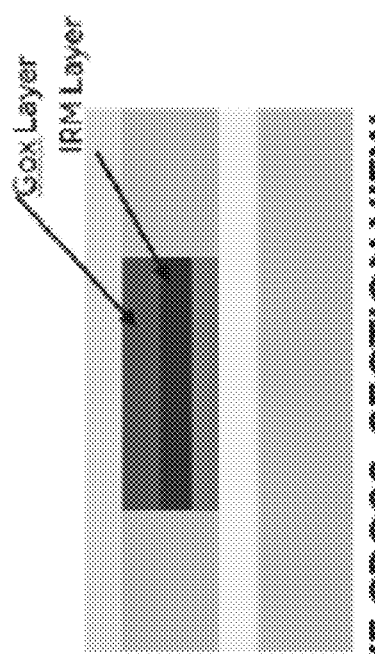
FIGURE 1C

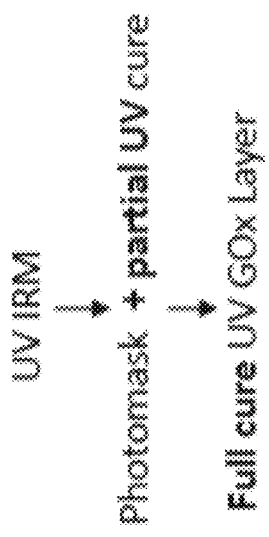
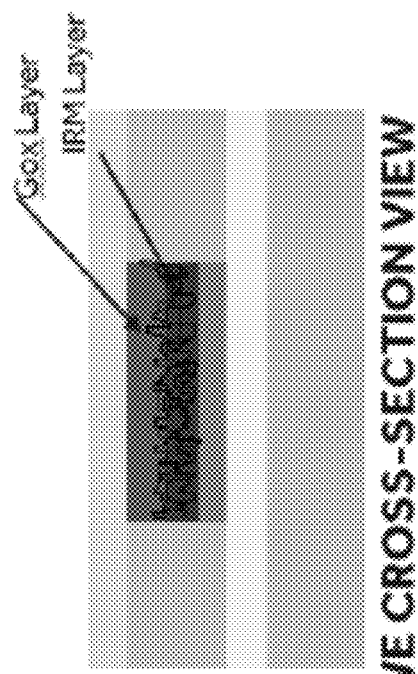
FIGURE 1D

FIG. 5

PARTIAL UV EXPOSURE

IRM Layer (made of Acrylate Monomer + X-linker)

↓

Partial UV Exposure to only partially cross-link the IRM layer

↓

Deposit Gox (spray of slot coat)

↓

Fully Cure the Gox layer (for selective deposition of Gox) and the UV light will penetrate to the layer below it thus fully curing the IRM layer as well

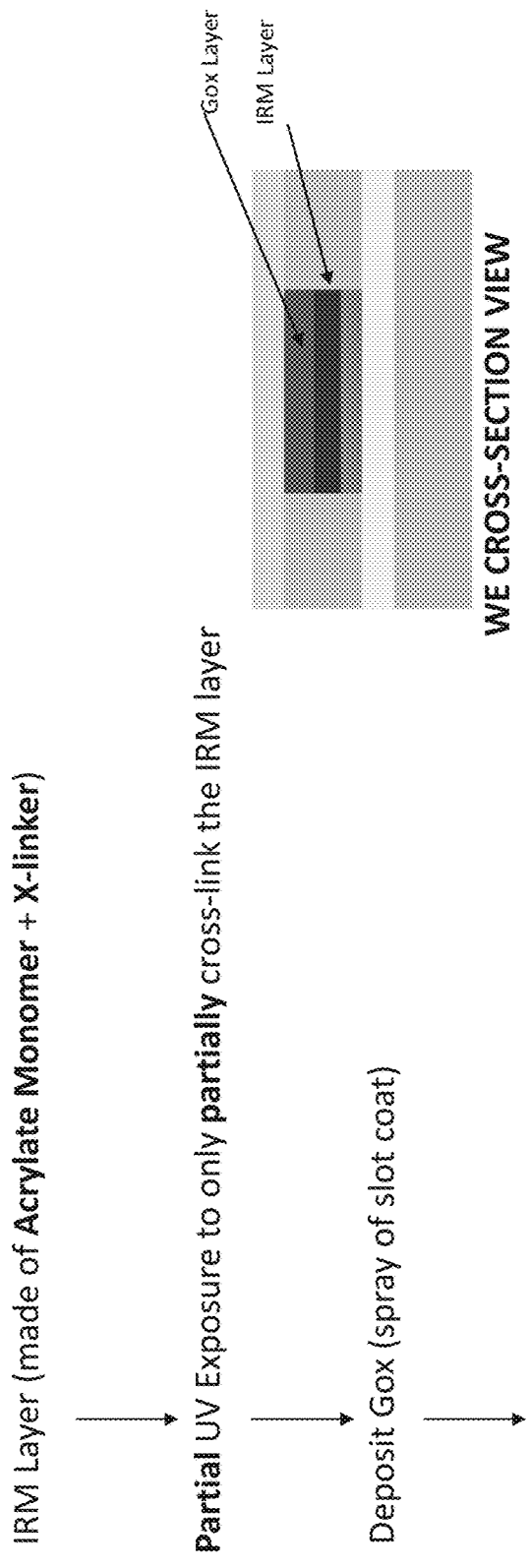

WE CROSS-SECTION VIEW

Acrylate Monomer examples that are biocompatible:

- Hema (Hydroxyethylmethacrylate)
- Mma (methyl methacrylate)
- Hydroxybutyl methacrylate

X-linkers examples:

- EGDA (Ethylene glycol diacetate)
- Poly(ethylene glycol) diacrylate with low molecular weight (e.g. 250)
- (3-Aminopropyl)triethoxysilane

FIG. 9
ASCORBIC ACID REJECTION MEMBRANE
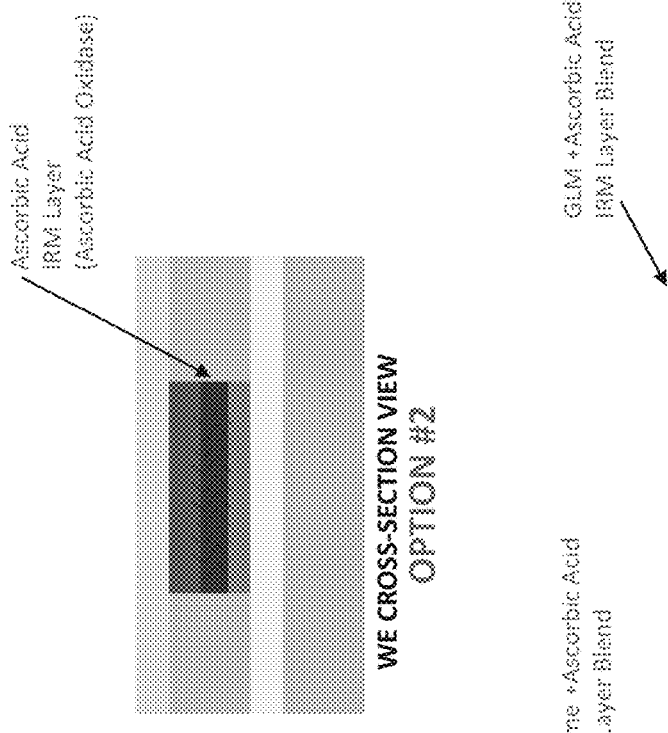
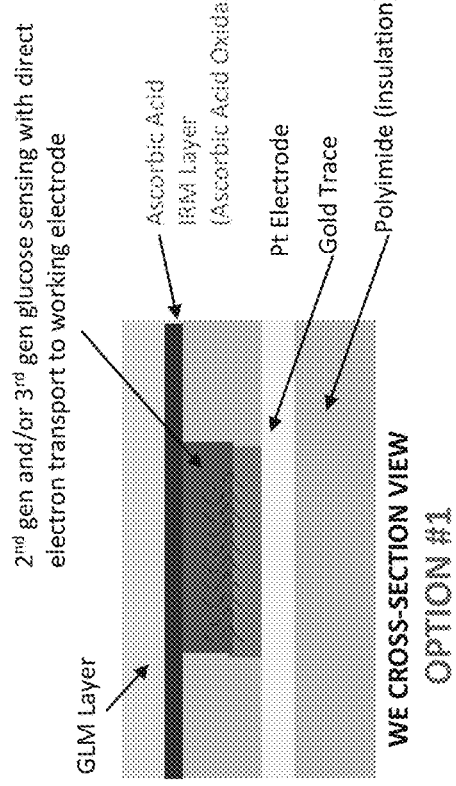
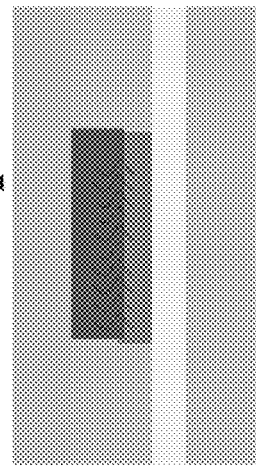
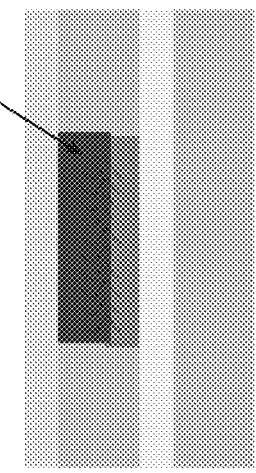

INTERFERENCE REJECTION MEMBRANES USEFUL WITH ANALYTE SENSORS

BACKGROUND OF THE INVENTION

1. Field of the Invention

This invention relates to methods and materials useful in making and using analyte sensors.

2. Description of Related Art

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

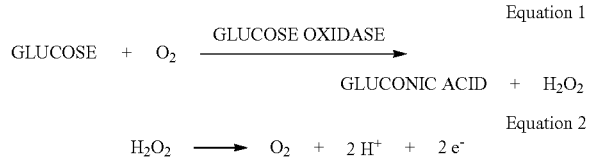

The glucose oxidase is used to catalyze the reaction between glucose and oxygen to yield gluconic acid and hydrogen peroxide (Equation 1). The $H_2O_2$ reacts electrochemically as shown in Equation 2, and the current can be measured by a potentiostat. These reactions, which occur in a variety of oxidoreductases known in the art, are used in a number of sensor designs.

One common problem with electrochemical sensors is that they can electrochemically react not only with the analyte to be measured (or by-product of the enzymatic reaction with the analyte), but can also react with other electroactive chemical species that are not intentionally being measured, which causes an increase in signal strength due to these "interfering species". Typically, such interfering species are compounds with an oxidation or reduction potential that overlaps with the analyte to be measured (or by-product of the enzymatic reaction with the analyte). For example, in a conventional amperometric glucose oxidase-based glucose sensor wherein the sensor measures hydrogen peroxide, interfering species such as acetaminophen, ascorbate, and urate are known to confound true analyte signals.

For the above-noted reasons, methods and materials designed to address the difficulties caused by such interfering species are desirable.

SUMMARY OF THE INVENTION

Interference rejection membranes (IRMs) are used in amperometric analyte sensors (e.g. glucose sensors commonly used by diabetic individuals) to prevent interferents such as acetaminophen and ascorbic acid from contacting working electrodes in such sensors and generating spurious electronic signals that do not reflect the presence of the sensor analyte. The use of such IRMs however can complicate the sensor manufacturing process, for example in situations where the IRM must be selectively coated on certain areas of a sensor (e.g. a working electrode) but not other areas (e.g. sensor electrical contact pads). Such limitations can make downstream sensor manufacturing processes such as process control monitors (PCM's) of other layered materials used to construct the sensor difficult. A solution to such problems that is disclosed herein includes new IRM chemistry formulations and associated methods which allow IRMs to be selectively deposited at precise sensor locations, for example. on a stack of layered materials disposed on a sensor electrode.

Embodiments of the invention provide compositions useful in analyte sensors as well as methods for making and using such compositions and analyte sensors. As discussed below, embodiments of the invention include IRMs comprising polymers such as a polyvinyl alcohol polymer or a Poly(2-hydroxyethyl methacrylate) polymer which are formed via a light mediated polymerization process (e.g. using an Azo polymerization initiator). In certain embodiments of the invention, the IRMs are crosslinked in situ, for example by a diacrylate crosslinking agent. Moreover, certain embodiments of the invention further include, for example, sensors having a first working electrode coated with an IRM of the invention and a second working electrode that is not coated with an IRM and/or a background electrode with no sensor coatings, wherein signals from these electrodes are compared in order to characterize signals from interfering agents (such as acetaminophen). In this way, embodiments of the invention can be used, for example, to better track patient compliance to prescribed drugs. In addition, embodiments of the invention can, for example, be used to facilitate the calibration of amperometric analyte sensors.

Typical embodiments of the invention include methods of making amperometric analyte sensors for implantation within a mammal, methods where these sensors are designed to include improved IRM compositions and sensor configurations. Such methods typically include the steps of providing a first base layer (e.g. a base comprising a flexible sensor substrate); forming a conductive layer on the first base layer, wherein the conductive layer includes a first working electrode (and typically additional electrodes such as a counter and reference electrode); forming an analyte sensing layer on the conductive layer, wherein the analyte sensing layer includes an enzyme selected to generate a detectable electrical signal upon exposure to an analyte (e.g. glucose oxidase, cellobiose dehydrogenase or the like); and then forming an interference rejection layer on the analyte sensing layer. Typically in such methods, the interference rejection layer is formed in situ on an electrode or a stack of layered sensor materials by a reaction mixture comprising a polymerizable monomer, a crosslinking agent and a photoinitiator agent; and the interference rejection layer is formed when the reaction mixture is polymerized by exposure to light. These methods further comprise forming an analyte modulating layer in situ on the interference rejection layer; such that an amperometric analyte sensor for implantation within a mammal is made. In certain methodological embodiments designed, for example, to facilitate sensor layer adhesion, the analyte sensing layer of the sensor is also formed by a reaction mixture comprising a polymerizable monomer, a crosslinking agent and a photoinitiator agent and the analyte sensing layer is formed when the reaction mixture is polymerized by exposure to light.

In certain embodiments of the invention, an IRM reaction mixture used to make the amperometric analyte sensor forms a polyvinyl alcohol polymer or a poly(2-hydroxyethyl methacrylate) polymer. Typically, a polymer in the IRM is crosslinked. In illustrative embodiments of the invention, an IRM reaction mixture used to make the amperometric analyte sensor includes an polymerizable monomer comprising a hydroxyethylmethacrylate monomer, a methyl methacrylate monomer and/or a hydroxybutyl methacrylate monomer; and/or the crosslinking agent comprises an ethylene glycol (e.g. an ethylene glycol diacrylate crosslinking agent) and/or a silane; and/or the photoinitiator agent comprises a diazo photoinitiator compound. In certain embodiments of the invention, the amperometric analyte sensor comprises additional constituents/layers such as a layer comprising the enzyme ascorbic acid oxidase. In some embodiments of the invention, the ascorbic acid oxidase is not disposed within an IRM and can be disposed with another functional layer of the sensor, for example the analyte limiting layer or the analyte sensing layer. For example, embodiments of the invention include those where the layer comprising the ascorbic acid oxidase enzyme comprises glucose oxidase or comprises an analyte modulating layer as well as embodiments where the layer comprising an ascorbic acid oxidase enzyme does not comprise glucose oxidase or does not comprise an analyte modulating layer. Alternatively, the ascorbic acid oxidase is disposed in a separate layer.

In some methodological embodiments of the invention, the interference rejection layer (and/or the analyte sensing layer) is formed in a single step comprising exposure to light. In other embodiments of the invention, the interference rejection layer (and/or the analyte sensing layer) is formed in a plurality of steps comprising exposure to light. For example, methods that use a plurality of steps comprising exposure to light can comprise a first exposure to light selected to partially polymerize the interference rejection reaction mixture comprising a polymerizable monomer, a crosslinking agent and a photoinitiator agent; and then second exposure to light selected to fully polymerize the analyte sensing reaction mixture comprising a polymerizable monomer, a crosslinking agent and a photoinitiator agent; as well as to cure the partially polymerized interference rejection reaction mixture formed by the first exposure to light. In certain embodiments of the invention, at least one interference rejection reaction mixture is selectively disposed on a location on the base and/or one photomask is used to selectively polymerize an interference rejection reaction mixture disposed on the base at particular locations, for example so that contact pads and/or conductor traces disposed on the base do not comprise an interference rejection layer/composition.

The amperometric analyte sensors disclosed herein can be formed to have a number of different configurations in order to, for example, better monitor patient physiology. For example, in some embodiments of the invention, the conductive layer is formed to include a second working electrode that comprises an analyte sensing layer and an analyte modulating layer; and does not comprise an interference rejection layer. In some embodiments of the invention, the conductive layer is formed to include a background electrode, wherein said background electrode does not comprise an analyte sensing layer, an analyte modulating layer; and an interference rejection layer. Such embodiments of the invention are designed so that the signal from interferents such as drugs (such as acetaminophen) can be characterized in order to better assess patient physiology. In particular, compliance with medical recommendations, especially, with compliance to taking prescribed drugs is a complex challenge within any medical field, but can be particularly complex with diabetic patients that often have other comorbidities. Solution to such problems that are disclosed herein include using sensor embodiments where one working electrode is coated with IRM and another working electrode is not coated with an IRM (optionally such sensors can further include a background electrode with no sensor coatings), so that the signal from interfering agents such as drugs (such as acetaminophen) can be detected in order to better assess patient physiology and, for example, to track patient compliance in taking certain drugs.

Embodiments of the invention include amperometric analyte sensors having the interference rejection membranes and/or formed from the associated methods disclosed herein. Typically such amperometric analyte sensors include a first base layer (e.g. one comprising a flexible substrate element); a conductive layer disposed on the first base layer, wherein the conductive layer includes a first working electrode (and typically additional electrodes such as a counter and reference electrode); an analyte sensing layer comprising an enzyme selected to generate a detectable electrical signal upon exposure to glucose (e.g. glucose oxidase, cellobiose dehydrogenase or the like) disposed on the working electrode; and an interference rejection layer disposed on the analyte sensing layer. In such amperometric analyte sensors, the interference rejection layer is formed by a reaction mixture comprising a polymerizable monomer, a crosslinking agent and a photoinitiator agent; and the interference rejection layer is cured when the reaction mixture is polymerized by exposure to light, either in single curing steps or curing steps comprising multiple exposures to light. Such amperometric analyte sensors further include an analyte modulating layer disposed on the interference rejection layer. Optionally, the analyte sensing layer is also formed by a reaction mixture comprising a polymerizable a monomer, a crosslinking agent and a photoinitiator agent and the analyte sensing layer is formed when the reaction mixture is polymerized by exposure to light. In certain sensor embodiments, contact pads and/or conductor traces disposed on the base do not comprise an interference rejection layer. In some sensor embodiments, the sensor comprises additional constituents/layers such as a layer comprising an ascorbic acid oxidase.

As discussed below, additional embodiments of the invention include methods of sensing an analyte within the body of a mammal, the methods comprising: implanting an electrochemical analyte sensor disclosed herein into the mammal; sensing an alteration in current at the working electrode in the presence of the analyte; and then correlating the alteration in current with the presence of the analyte, so that the analyte is sensed. In some amperometric analyte sensor embodiments designed to more precisely observe patient physiology, the conductive layer includes a second working electrode comprising the analyte sensing layer and the analyte modulating layer and does not include the interference rejection layer; and glucose is sensed by comparing an electrical signal at the first working electrode in the presence of glucose with an electrical signal at the second working electrode in the presence of glucose. In related amperometric analyte sensor embodiments, the conductive layer further includes a background electrode that does not comprise an analyte sensing layer, an analyte modulating layer; or an interference rejection layer; and glucose is sensed by comparing an electrical signal at the first working electrode in the presence of glucose with an electrical signal at the background electrode in the presence of glucose.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

FIGS. 1A-1F provides schematics and data showing illustrative chemical reactions for forming interference rejection membrane compositions of the invention (FIG. 1A and FIG. 1B); illustrative curing processes for forming interference rejection membrane composition layers (FIG. 1C and FIG. 1D); a schematic of a flexible sensor substrate having a number of electrodes disposed thereon (FIG. 1E) and data from a sensor that includes an IRM of the invention (FIG. 1F).

FIG. 5 provides a flow chart (left panel) and a schematic cross section (right panel) of a an embodiment of one method for making interference rejection membrane (IRM). This methodological embodiment of a deposition process involves partial UV exposure of the IRM reaction mixture (to partially polymerize components in this mixture), followed by deposition of the analyte sensing layer (comprising glucose oxidase, GOx), and then a subsequent UV exposure of the IRM and analyte sensing layer reaction mixtures to fully cure both the IRM and the analyte sensing layer reaction mixtures (as compared to methodological embodiments where the IRM is fully cured in a single step). Illustrative components of one embodiment of an IRM useful in such embodiments of the invention are included at the bottom of the figure.

FIG. 7B provides a schematic showing how signals can be compared from the two working electrodes, one of which is coated with an IRM and other of which is not.

FIG. 8B provides a schematic showing how signals can be compared from the background electrode and the two working electrodes, one of which is coated with an IRM and other of which is not.

FIG. 9 provides schematic of embodiments of the invention where the amperometric analyte sensor includes a layer comprising an ascorbic acid oxidase.

DETAILED DESCRIPTION OF THE EMBODIMENTS

Figure 1A:
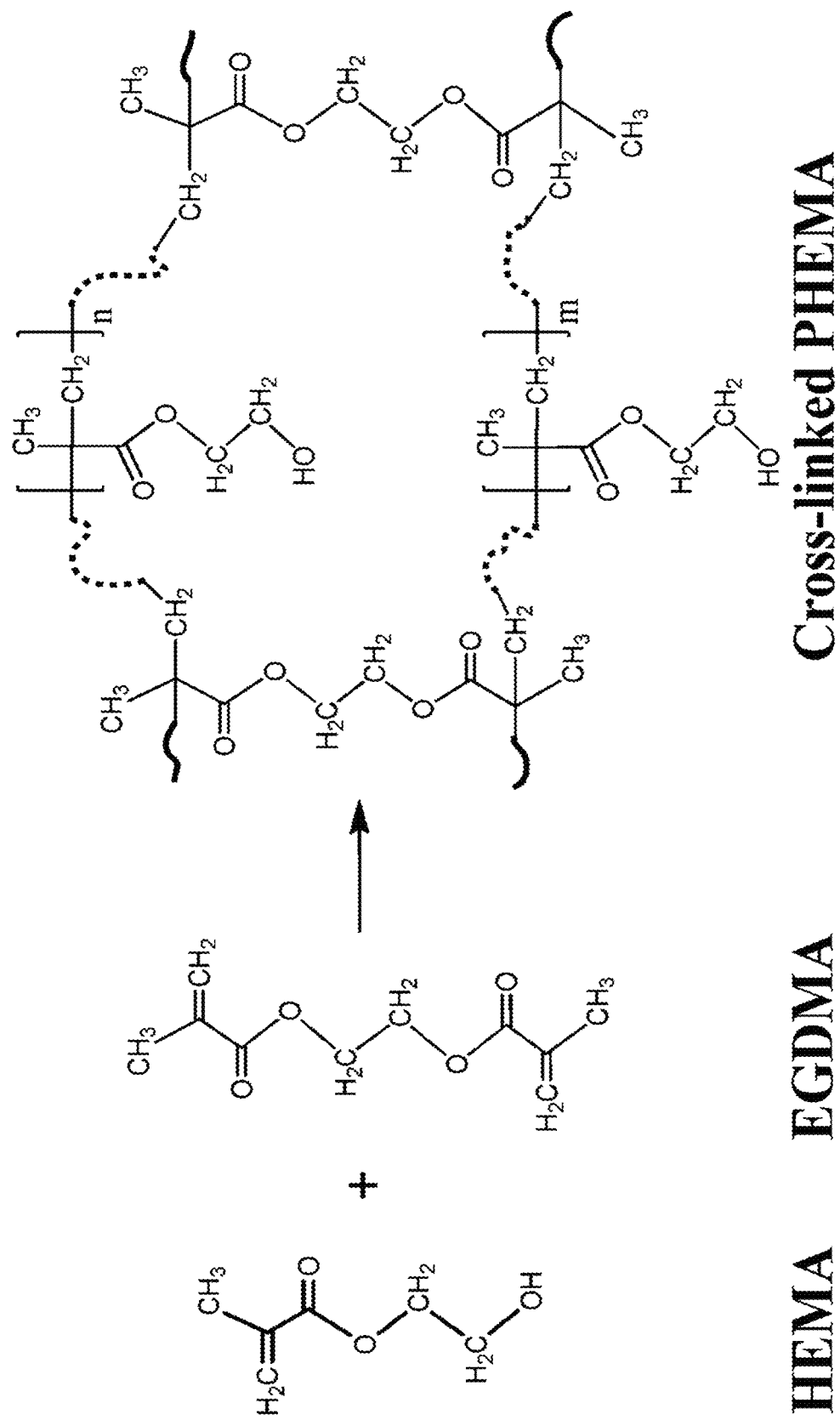

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

It must be noted that as used herein and in the appended claims, the singular forms "a", "and", and "the" include plural referents unless the context clearly dictates otherwise. Thus, for example, reference to "an oxidoreductase"

includes a plurality of such oxidoreductases and equivalents thereof known to those skilled in the art, and so forth. All numbers recited in the specification and associated claims that refer to values that can be numerically characterized with a value other than a whole number (e.g. "50 mol %") are understood to be modified by the term "about".

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

As discussed in detail below, embodiments of the invention relate to the use of an electrochemical sensor that exhibits a novel constellation of material and functional elements. Such sensors use layered polymeric compositions in order to form, for example, analyte sensors having a unique set of technically desirable material properties including biocompatibility as well as addressing problems in this art that result, for example, from the presence of in vivo substances (e.g. ascorbic acid and acetaminophen) that interfere with analyte signals. The electrochemical sensor embodiments of the invention are designed to measure a concentration of an analyte of interest (e.g. glucose) or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors comprise a polymeric membrane surrounding the enzyme through which an analyte migrates prior to reacting with the enzyme. The product is then measured using electrochemical methods and thus the output of an electrode system functions as a measure of the analyte. In some embodiments, the sensor can use an amperometric, coulometric, conductometric, and/or potentiometric technique for measuring the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042625, and WO 03/074107, and European Patent Application EP 1153571, the contents of each of which are incorporated herein by reference.

As discussed in detail below, embodiments of the invention disclosed herein provide sensor elements having enhanced material properties and/or architectural configurations and sensor systems (e.g. those comprising a sensor and associated electronic components such as a monitor, a processor and the like) constructed to include such elements. The disclosure further provides methods for making and using such sensor membranes and/or architectural configurations. While some embodiments of the invention pertain to glucose sensors, a variety of the elements disclosed herein (e.g. polymeric compositions comprising interference rejection membranes/layers) can be adapted for use with any one of the wide variety of sensors and other implantable medical devices known in the art. The analyte sensor elements, architectures and methods for making and using these elements that are disclosed herein can be used to establish a variety of layered sensor structures.

Specific aspects of embodiments of the invention are discussed in detail in the following sections.

Typical Elements, Configurations and Analyte Sensors of the Invention

Optimized Sensor Elements of the Invention

Embodiments of the invention provide compositions useful in analyte sensors as well as methods for making and using such compositions and analyte sensors. Typical embodiments of the invention include methods of making an amperometric analyte sensor for implantation within a mammal. Such methods typically include the steps of providing a first base layer (e.g. a base comprising a flexible substrate formed from a polymeric material); forming a conductive layer on the first base layer, wherein the conductive layer includes a first working electrode; forming an analyte sensing layer on the conductive layer, wherein the analyte sensing layer includes an enzyme selected to generate a detectable electrical signal upon exposure to an analyte (e.g. glucose oxidase); and then forming an interference rejection layer on the analyte sensing layer. In such methods, the interference rejection layer is formed by a reaction mixture comprising a polymerizable monomer, a crosslinking agent and a photoinitiator agent; and the interference rejection layer is formed when the reaction mixture is polymerized by exposure to light. While polymerizable acrylate monomers are used in various descriptions of the invention, those of skill in the art understand that a variety of polymerizable monomers can be used to form the IRMs of the invention. These methods further comprise forming an analyte modulating layer on the interference rejection layer; such that an amperometric analyte sensor for implantation within a mammal is made.

In certain embodiments of the invention, the relative amounts or ratios of crosslinking agent and polymerizable acrylate monomer disposed within an IRM reaction mixture (or a glucose limiting membrane layer reaction mixture or an analyte sensing layer reaction mixture) are selected such that the reaction mixture comprises about a 15 to 96% of crosslinker to monomer ratio (and typically about a 50%-80% crosslinker to monomer ratio). In some embodiments of the invention, the relative amounts of crosslinking agent (an ethylene glycol diacrylate crosslinking agent) and polymerizable acrylate monomer (e.g. a polyHema acrylate monomer) disposed within the reaction mixture is selected such that the reaction mixture comprises about 50%-80% crosslinking agent and about 20%-50% polymerizable acrylate monomer. In this context, by changing the crosslinker to monomer ratio, material characteristics such as the permeability of the membrane (e.g. mesh size) can be adjusted. For example, ratios that include more crosslinkers can be used to decrease the permeability of the membrane (see, e.g. Kermis et al., Journal of Membrane Science 212 (2003) 75-86). Certain reagents and methods than can be adapted for use with the invention are also described in Wong, Eng. Life Sci. 2011, 11, No. 1, 20-25. In illustrative embodiments of the invention, the IRM reaction mixture includes an acrylate monomer comprising a hydroxyethylmethacrylate monomer, a methyl methacrylate monomer and/or a hydroxybutyl methacrylate monomer; and/or the crosslinking agent comprises an ethylene glycol and/or a silane (see, e.g. FIGS. 1 and 5). In some embodiments of the invention, the IRM (or other layer) reaction mixture can comprises one or more vinyl methyacrylates, methyl methacrylates, ethylene glycol diacrylates, Tetra(ethylene glycol) diacrylates, low MW Poly(ethylene glycol) diacrylates, allyl methacrylates or allyl acrylates.

In certain embodiments of the invention, the stack of layered materials within the amperometric analyte sensor includes a layer comprising an ascorbic acid oxidase that breaks down ascorbic acid (see, e.g., FIG. 9). Typically in such embodiments, an IRM layer in the sensor is disposed between the electrode surface and the layer comprising the ascorbic acid oxidase (e.g. the layer comprising the ascorbic acid oxidase is disposed directly or indirectly over or on top of the IRM layer so that agents such as ascorbic acid that are present in an in vivo environment encounter the layer comprising an ascorbic acid oxidase prior to encountering the IRM). In certain embodiments of the invention, the ascorbic acid oxidase is disposed in an analyte sensing membrane/layer (e.g. one also comprising glucose oxidase) or an analyte limiting membrane/layer. In some embodiments of the invention, the ascorbic acid oxidase is not disposed in the IRM layer. Methods and materials useful to make such layers a known in the art and described, for example, in Bi et al., Sensors and Actuators B: Chemical Volume 224, 1 Mar. 2016, Pages 668-675; Imato et al., Sensors and Actuators B: Chemical Volume 13, Issues 1-3, May 1993, Pages 68-72; and Guo et al., Photonic Sensors, 2019, DOI: 10.1007/s13320-020-0605-2.

Optionally the analyte sensing layer of the sensor is also formed by a reaction mixture comprising a polymerizable acrylate monomer, a crosslinking agent and a photoinitiator agent and the analyte sensing layer is formed when the reaction mixture is polymerized by exposure to light (see, e.g. FIG. 5). In this context, a variety of conventional deposition methods can be adapted to deposit the IRM compositions and the compositions of the other layers including screen-printing processes, shadow masking processes, lift-off processes, aerosol jet processes, selective dispensing processes and the like.

In some embodiments of the invention, the interference rejection layer (and/or the analyte sensing layer) is formed in a single step comprising exposure to light. In other embodiments of the invention, the interference rejection layer (and/or the analyte sensing layer) is formed in a plurality of steps comprising exposure to light (see, e.g. FIG. 5). For example, the plurality of steps comprising exposure to light can comprise a first exposure to light selected to partially polymerize the interference rejection reaction mixture comprising a polymerizable acrylate monomer, a crosslinking agent and a photoinitiator agent; and then second exposure to light selected to fully polymerize the analyte sensing reaction mixture comprising a polymerizable acrylate monomer, a crosslinking agent and a photoinitiator agent; as well as the partially polymerized interference rejection reaction mixture. The formulations disclosed herein allow IRM to be selectively deposited at various sensor locations such as on a sensor. In certain embodiments of the invention, at least one interference rejection reaction mixture is selectively disposed on a location on the base and/or one photomask is used to selectively polymerize an interference rejection reaction mixture disposed on the base, for example so that contact pads and/or conductor traces disposed on the base do not comprise an interference rejection layer.

The sensors disclosed herein can be formed to have a number of different configurations. For example, in some embodiments of the invention, the conductive layer is formed to include a second working electrode that comprises an analyte sensing layer and an analyte modulating layer; and does not comprise an interference rejection layer. In some embodiments of the invention, the conductive layer is formed to include a background electrode, wherein said background electrode does not comprise an analyte sensing layer, an analyte modulating layer; and an interference rejection layer.

Embodiments of the invention include amperometric analyte sensors formed from the methods disclosed herein. Illustrative sensor embodiments of the inventions are shown in FIGS. 3-9. Typically such amperometric analyte sensors include a first base layer (e.g. one comprising a flexible substrate element); a conductive layer disposed on the first base layer, wherein the conductive layer includes a first working electrode; an analyte sensing layer comprising an enzyme selected to generate a detectable electrical signal upon exposure to glucose disposed on the working electrode; and an interference rejection layer disposed on the analyte sensing layer. In such amperometric analyte sensors, the interference rejection layer is formed by a reaction mixture comprising a polymerizable acrylate monomer, a crosslinking agent and a photoinitiator agent; and the interference rejection layer is cured when the reaction mixture is polymerized by exposure to light, either in single curing steps or curing steps comprising multiple exposures to light. Typically in such sensor layers, the acrylate monomer comprises a hydroxyethylmethacrylate monomer, a methyl methacrylate monomer and/or a hydroxybutyl methacrylate monomer; and the crosslinking agent comprises an ethylene glycol and/or a silane.

Embodiments of the invention can be adapted use art accepted methods and materials such as those disclosed in Abdul-Aziz et al., Engineering in Life Sciences Volume 11, Issue 1, January 2011, the contents of which are incorporated by reference herein. Azo polymerization initiators are compounds having an azo group (R—N=N—R'), which decompose with heat and/or light, and forms carbon radical. The formed carbon radical is excellent in reactivity, and progresses polymerization and halogenation reactions of different types of monomers. Illustrative diazo based IRM compositions of the invention include, for example, IRM compositions formed in the following manner: 8 g diazo sensitizer (benzenediazonium, 4-(phenylamino)-, sulfate (1:1), polymer with formaldehyde, CAS: 41432-19-3, Charkit product Code: KB-11S) was dissolved in 200 mL H2O. 1 mL of the prepared diazo solution was added to 5 g (5% Polyvinyl alcohol). The solution was spin-coated @300-600 rpm onto sensor plates before GOX layer deposition. This layer was then cured using UV (350-405 nm) @7-9 mw/cm2 UV intensity for 99 s. The plate was heated after UV exposure at the oven for 5-10 minutes at 150-175° C., then rinsed in H2O to wash off the non-crosslinked chemicals. In another IRM embodiment of the invention, 2-Hydroxyethyl methacrylate (HEMA) monomer, ethylene glycol dimethacrylate (EGDMA) was used as a crosslinker, and 2,2-dimethoxy-2-phenylacetophenone (DMPP) was used as photoinitiator. In this embodiment, 5-90 vol % HEMA in water was mixed with EGDMA (5-90 mol % wt. HEMA monomer). The material was then coated on a substrate by spin coating at 100-800 rpm (alternatively such materials can be spray coated). For both of these types of IRMS, photomasks can be used for the selective curing of the material so that it is disposed at a particular location (s), for example only on the working electrode.

Typically, the amperometric analyte sensors of the invention further include an analyte modulating layer disposed on the interference rejection layer. Optionally, the analyte sensing layer is formed by a reaction mixture comprising a polymerizable acrylate monomer, a crosslinking agent and a photoinitiator agent and the analyte sensing layer is formed when the reaction mixture is polymerized by exposure to light. In certain sensor embodiments, contact pads and/or conductor traces disposed on the base do not comprise an interference rejection layer. In some sensor embodiments, a sensor layer comprises an ascorbic acid oxidase. Such sensor embodiments are useful with sensors that may be prone to interference from other more common interferents such as ascorbic acid (Vitamin-C). In certain embodiments of the invention, the analyte sensing layer, the interference rejection layer or the analyte modulating layer comprises: a diisocyanate; a hydrophilic polymer comprising a hydrophilic diol or hydrophilic diamine; a siloxane having an amino, hydroxyl or carboxylic acid functional group at a terminus; or a polycarbonate diol. In certain methods of making an analyte sensor for implantation within a mammal, the diisocyanate comprises a hexamethylene diisocyanate and/or a methylene diphenyl diisocyanate, the JEFFAMINE comprises about 45% JEFFAMINE 600 and/or JEFFAMINE 900, the polydimethylsiloxane comprises about 22.5% polydimethylsiloxane-A15), and the polycarbonate diol comprises about 7.5% (poly(1,6-hexyle carbonate) diol. Typically in this embodiment, the catalyst (e.g. Dibutyltin bis(2-ethylhexanoate)) is present in the reaction mixture in amounts less than 0.19%, 0.17%, 0.15%, 0.13%, or 0.11% of the reaction mixture (e.g. about 0.1%).

Figure 8A:
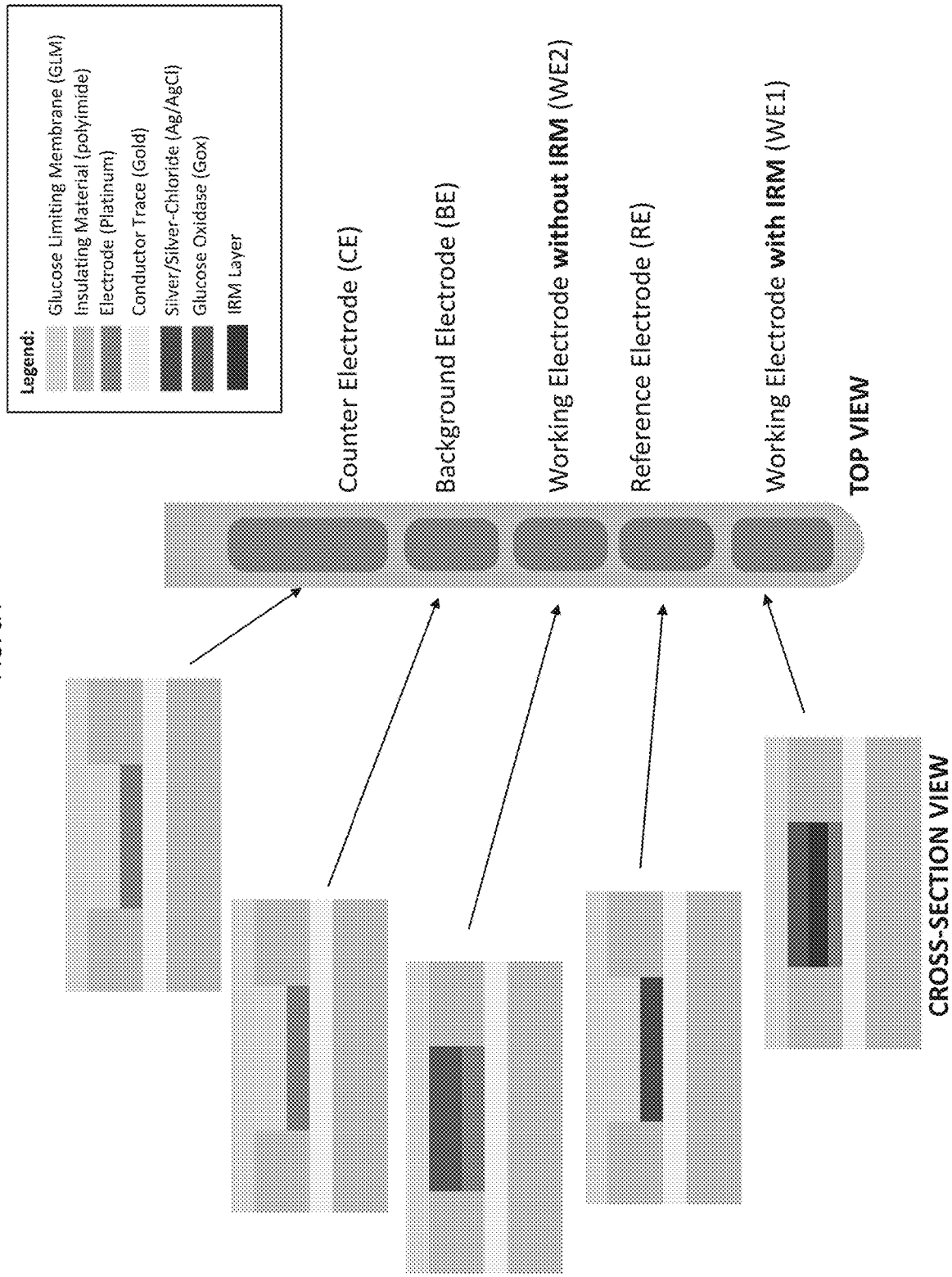
FIGS. 8A and 8B provide schematics of a sensor embodiment having two working electrodes, one of which is coated with an IRM and one of which is not, as well as a background electrode. The right panel in FIG. 8A shows cross-sectional views of materials deposited on a counter, reference, background and two working electrodes of a sensor disposed on a longitudinal member as shown in the left panel (e.g. a sensor flex element).
Figure 8B:
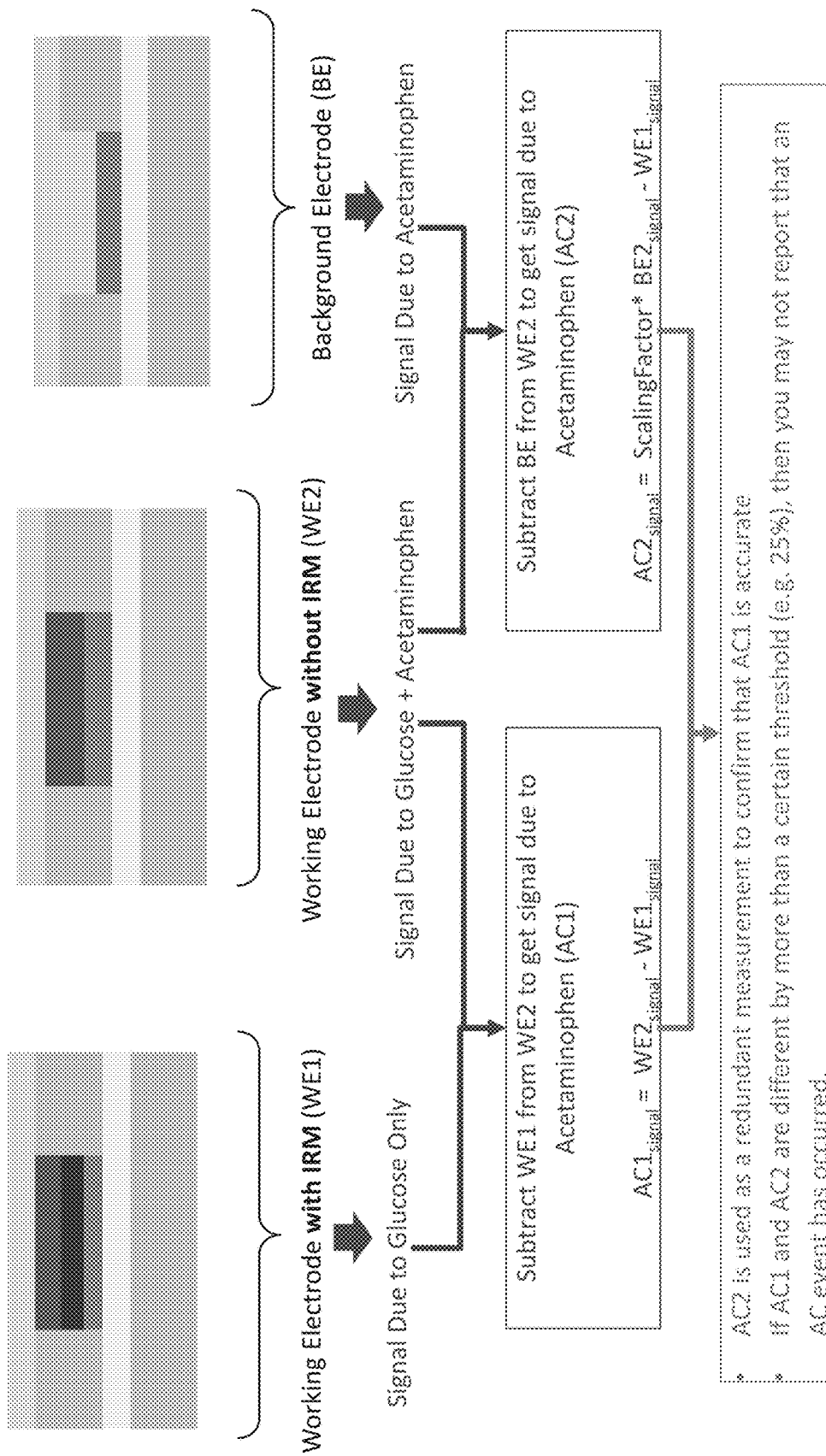

In some amperometric analyte sensor embodiments, the conductive layer includes a second working electrode comprising the analyte sensing layer and the analyte modulating layer and does not include the interference rejection layer; and glucose is sensed by comparing an electrical signal at the first working electrode in the presence of glucose with an electrical signal at the second working electrode in the presence of glucose (see, e.g. FIG. 8A). In some amperometric analyte sensor embodiments, the conductive layer includes a background electrode that does not comprise an analyte sensing layer, an analyte modulating layer; or an interference rejection layer; and glucose is sensed by comparing an electrical signal at the first working electrode in the presence of glucose with an electrical signal at the background electrode in the presence of glucose (see, e.g. FIG. 8B).

As discussed below, in certain embodiments, the amperometric analyte sensor further includes at least one of: an adhesion promoting layer; a protein layer; a layer comprising poly-1-lysine polymers having molecular weights between 30 KDa and 300 KDa; and a cover layer disposed on the analyte sensor apparatus, wherein the cover layer comprises an aperture positioned on the cover layer so as to facilitate an analyte present in an in vivo environment from contacting and diffusing through an analyte modulating layer; and contacting the analyte sensing layer.

As discussed below, additional embodiments of the invention include methods of sensing an analyte within the body of a mammal, the methods comprising: implanting an electrochemical analyte sensor disclosed herein into the mammal; sensing an alteration in current at the working electrode in the presence of the analyte; and then correlating the alteration in current with the presence of the analyte, so that the analyte is sensed. In some amperometric analyte sensor embodiments and methods for sensing glucose that are designed to more precisely observe patient physiology, the conductive layer includes a second working electrode comprising the analyte sensing layer and the analyte modulating layer and does not include the interference rejection layer; and glucose is sensed by comparing an electrical signal at the first working electrode in the presence of glucose with an electrical signal at the second working electrode in the presence of glucose. In related amperometric analyte sensor embodiments and methods of sensing glucose, the conductive layer further includes a background electrode that does not comprise an analyte sensing layer, an analyte modulating layer; or an interference rejection layer; and glucose is sensed by comparing an electrical signal at the first working electrode in the presence of glucose with an electrical signal at the background electrode in the presence of glucose.

As noted above, embodiments of the invention include sensor membranes made from polymeric reaction mixtures formed to include IRMs that inhibit signals from interfering species such as acetaminophen while simultaneously being more permeable to $O_2$ than to glucose. As is known in the art, a polymer comprises a long or larger molecule consisting of a chain or network of many repeating units, formed by chemically bonding together many identical or similar small molecules called monomers. A copolymer or heteropolymer is a polymer derived from two (or more) monomeric species, as opposed to a homopolymer where only one monomer is used. Copolymers may also be described in terms of the existence of or arrangement of branches in the polymer structure. Linear copolymers consist of a single main chain whereas branched copolymers consist of a single main chain with one or more polymeric side chains. Sensor membranes made from polymeric compositions disclosed herein can optimize analyte sensor function including biocompatibility, sensor sensitivity, stability and hydration profiles. In addition, by optimizing the stoichiometry of reactant species over a range of sensor temperatures, the membranes disclosed herein can optimize the chemical reactions that produce the critical measurable signals that correlate with the levels of an analyte of interest (e.g. glucose). The following sections describe illustrative sensor elements, sensor configurations and methodological embodiments of the invention.

In typical embodiments, the analyte sensor is a glucose sensor that is implantable in vivo. Optionally, the analyte sensor further comprises at least one of: a protein layer disposed on the analyte sensing layer, or a cover layer disposed on the analyte sensor apparatus, and the cover layer comprises an aperture positioned on the cover layer so as to facilitate an analyte present in an in vivo environment from contacting and diffusing through an analyte modulating layer; and contacting the analyte sensing layer. In certain of these analyte sensors, the conductive layer comprises a plurality of electrodes including a working electrode, a counter electrode and a reference electrode, for example an embodiment where the conductive layer comprises a plurality of working electrodes and/or counter electrodes and/or reference electrodes; and optionally the plurality of working, counter and reference electrodes are grouped together as a unit and positionally distributed on the conductive layer in a repeating pattern of units.

Figure 2A:
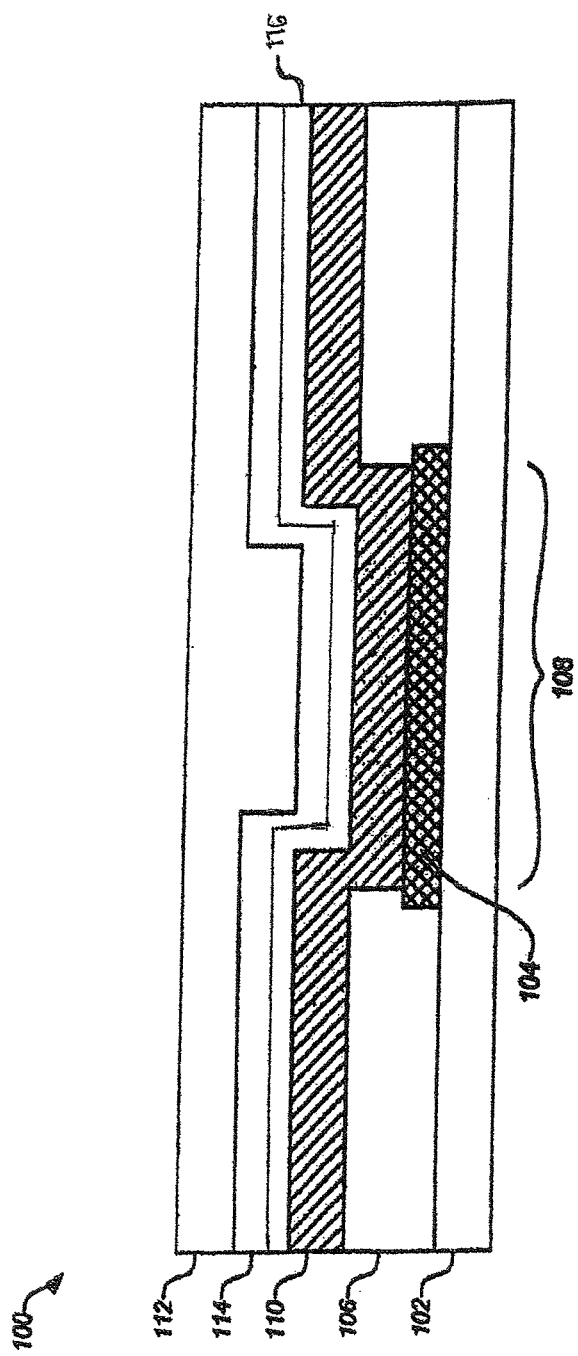
FIGS. 2A-2B provide schematics showing a conventional (PRIOR ART) sensor design comprising an amperometric analyte sensor formed from a plurality of planar layered elements which include albumin protein layer and an adhesion promoter layer (FIG. 2A); and a schematic showing differences between such conventional multilayer sensor stacks and sensor stacks having a high density amine layer (FIG. 2B).

Certain amperometric sensor design used with embodiments of the invention comprise a plurality of layered elements including for example a base layer having an electrode, an analyte sensing layer (e.g. one comprising glucose oxidase) and an analyte modulating layer in analyte diffusion control (e.g. to modulate the amounts of glucose and oxygen exposed to the analyte sensing layer). One such sensor embodiment is shown in FIG. 2A. Layered sensor designs that incorporate the polymeric compositions disclosed herein as the analyte modulating layer exhibit a constellation of material properties that overcome challenges observed in a variety of sensors including electrochemical glucose sensors that are implanted in vivo. For example, sensors designed to measure analytes in aqueous environments (e.g. those implanted in vivo) typically require wetting of the layers prior to and during the measurement of accurate analyte reading. Because the properties of a material can influence the rate at which it hydrates, the material properties of membranes used in aqueous environments ideally will facilitate sensor wetting to, for example, minimize the time period between the sensor's introduction into an aqueous environment and its ability to provide accurate signals that correspond to the concentrations of an analyte in that environment.

Moreover, with electrochemical glucose sensors that utilize the chemical reaction between glucose and glucose oxidase to generate a measurable signal, the material of the analyte modulating layer should not exacerbate (and ideally should diminish) what is known in the art as the "oxygen deficit problem". Specifically, because glucose oxidase-based sensors require both oxygen ($O_2$) as well as glucose to generate a signal, the presence of an excess of oxygen relative to glucose, is necessary for the operation of a glucose oxidase-based glucose sensor. However, because the concentration of oxygen in subcutaneous tissue is much less than that of glucose, oxygen can be the limiting reactant in the reaction between glucose, oxygen, and glucose oxidase in a sensor, a situation which compromises the sensor's ability to produce a signal that is strictly dependent on the concentration of glucose. In this context, because the properties of a material can influence the rate at which compounds diffuse through that material to the site of a measurable chemical reaction, the material properties of an analyte modulating layer used in electrochemical glucose sensors that utilize the chemical reaction between glucose and glucose oxidase to generate a measurable signal, should not for example, favor the diffusion of glucose over oxygen in a manner that contributes to the oxygen deficit problem. Embodiments of the invention that comprise the polymeric compositions do not contribute to, and instead function to ameliorate, the oxygen deficit problem. Typically for example, the analyte modulating layer is formed to exhibit a first permeability to glucose and a second permeability to $O_2$, and the permeability to $O_2$ is greater than the permeability to glucose.

Figure 1E:
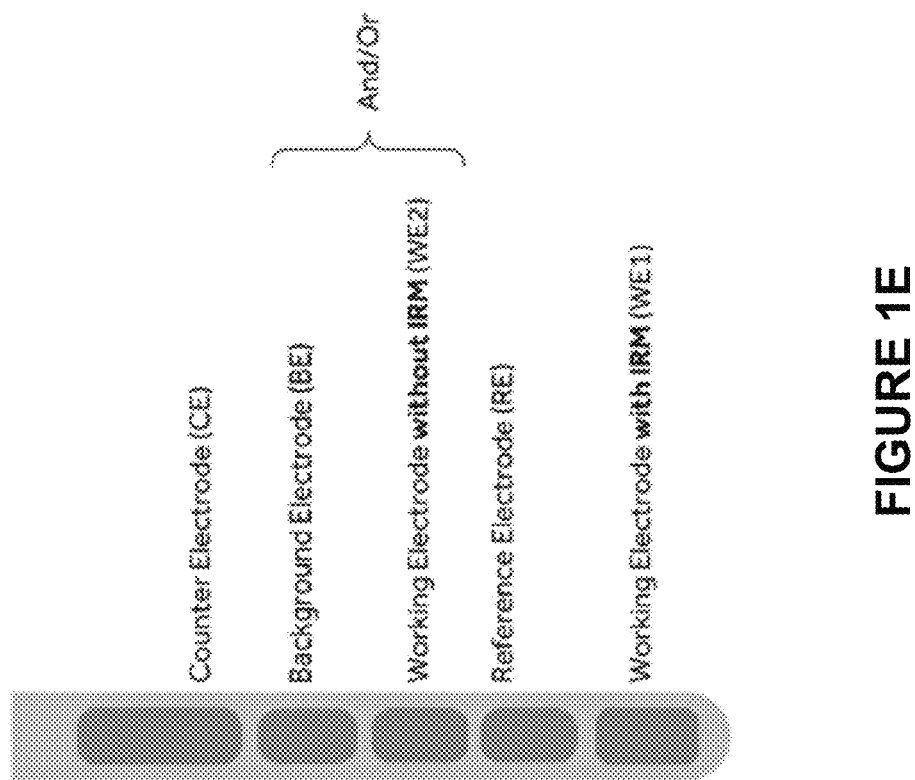
Figure 1F:
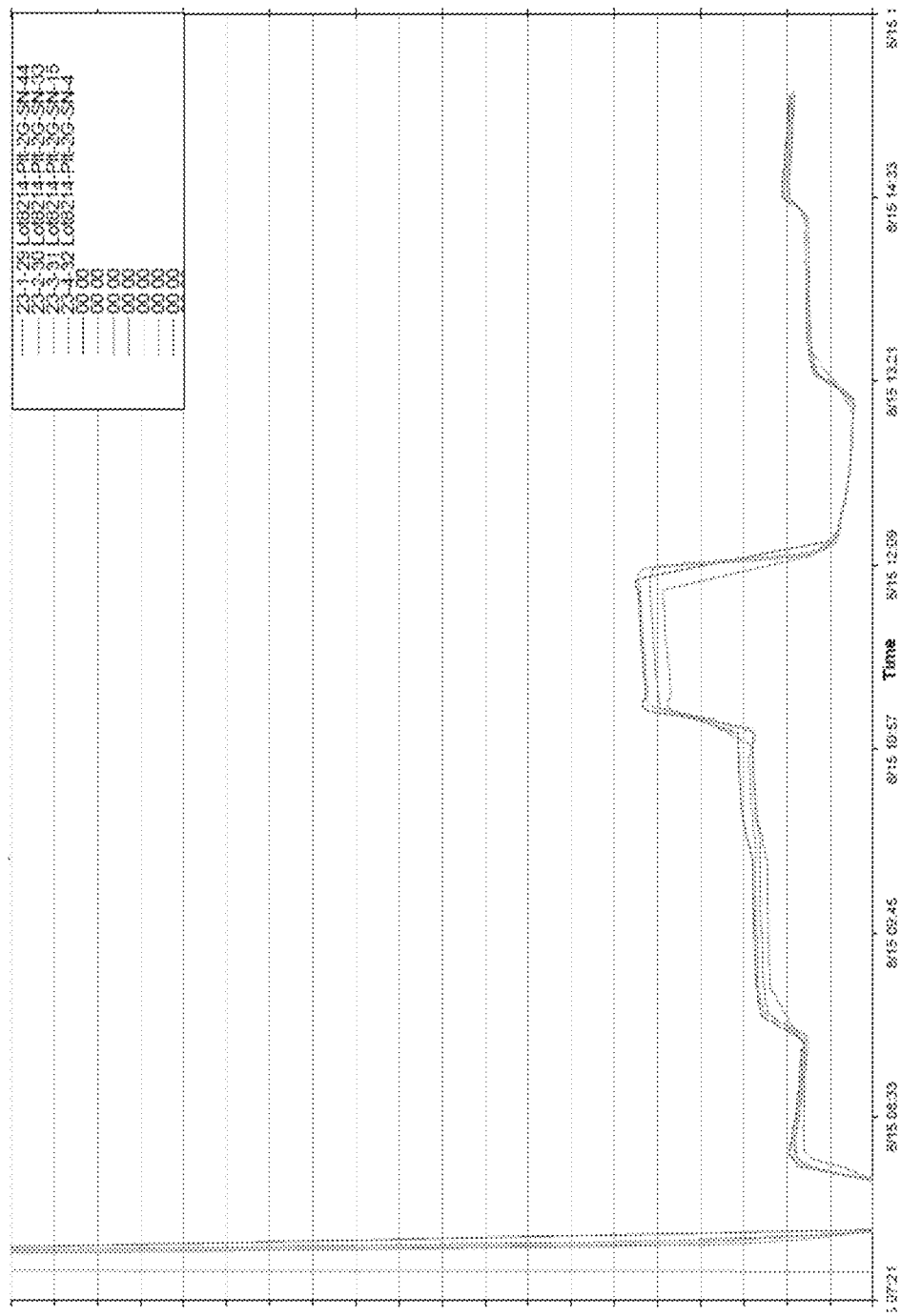

Embodiments of the invention include both materials (e.g. polymeric compositions compositions) as well as architectures that designed to facilitate sensor performance. For example, in certain embodiments of the invention, the conductive layer is formed on a flexible sensor base (e.g. a sensor flex assembly shown in FIGS. 2 and 8A) that comprises a plurality of working electrodes and/or counter electrodes and/or reference electrodes (e.g. 3 working electrodes, a reference electrode and a counter electrode), in order to, for example, avoid problems associated with poor sensor hydration and/or provide redundant sensing capabilities. Optionally, the plurality of working, counter and reference electrodes are configured together as a unit and positionally distributed on the conductive layer in a repeating pattern of units. In certain embodiments of the invention, the base layer comprises an architecture and is made from a flexible material (e.g. a longitudinal sensor flex element as shown in FIG. 1) that allows the sensor to twist and bend when implanted in vivo; and the electrodes are grouped in a configuration that facilitates an in vivo fluid contacting at least one of working electrode as the sensor apparatus twists and bends when implanted in vivo. In some embodiments, the electrodes are grouped in a configuration that allows the sensor to continue to function if a portion of the sensor having one or more electrodes is dislodged from an in vivo environment and exposed to an ex vivo environment. Typically, the sensor is operatively coupled to a sensor input capable of receiving a signal from the sensor that is based on a sensed analyte; and a processor coupled to the sensor input, wherein the processor is capable of characterizing one or more signals received from the sensor. In some embodiments of the invention, a pulsed voltage is used to obtain a signal from one or more electrodes of a sensor.

The sensors disclosed herein can be made from a wide variety of materials known in the art. In one illustrative embodiment of the invention, the analyte modulating layer comprises a polyurethane/polyurea polymer formed from a mixture comprising: a diisocyanate; a hydrophilic polymer comprising a hydrophilic diol or hydrophilic diamine; and a siloxane having an amino, hydroxyl or carboxylic acid functional group at a terminus; with this polymer then polycarbonate with a branched acrylate polymer formed from a mixture comprising: a butyl, propyl, ethyl or methyl-acrylate; an amino-acrylate; a siloxane-acrylate; and a poly(ethylene oxide)-acrylate. Optionally, additional materials can be included in these polymeric blends. For example, certain embodiments of the branched acrylate polymer are formed from a reaction mixture that includes a hydroxyl-acrylate compound (e.g. 2-hydroxyethyl methacrylate).

As used herein, the term "polyurethane/polyurea polymer" refers to a polymer containing urethane linkages, urea linkages or combinations thereof. As is known in the art, polyurethane is a polymer consisting of a chain of organic units joined by urethane (carbamate) links. Polyurethane polymers are typically formed through step-growth polymerization by reacting a monomer containing at least two isocyanate functional groups with another monomer containing at least two hydroxyl (alcohol) groups in the presence of a catalyst. Polyurea polymers are derived from the reaction product of an isocyanate component and a diamine. Typically, such polymers are formed by combining diisocyanates with alcohols and/or amines. For example, combining isophorone diisocyanate with PEG 600 and aminopropyl polysiloxane under polymerizing conditions provides a polyurethane/polyurea composition having both urethane (carbamate) linkages and urea linkages. Such polymers are well known in the art and described for example in U.S. Pat. Nos. 5,777,060, 5,882,494 and 6,632,015, and PCT publications WO 96/30431; WO 96/18115; WO 98/13685; and WO 98/17995, the contents of each of which is incorporated by reference.

The polyurethane/polyurea compositions of the invention are prepared from biologically acceptable polymers whose hydrophobic/hydrophilic balance can be varied over a wide range to control the ratio of the diffusion coefficient of oxygen to that of glucose, and to match this ratio to the design requirements of electrochemical glucose sensors intended for in vivo use. Such compositions can be prepared by conventional methods by the polymerization of monomers and polymers noted above. The resulting polymers are soluble in solvents such as acetone or ethanol and may be formed as a membrane from solution by dip, spray or spin coating.

Diisocyanates useful in this embodiment of the invention are those which are typically those which are used in the preparation of biocompatible polyurethanes. Such diisocyanates are described in detail in Szycher, SEMINAR ON ADVANCES IN MEDICAL GRADE POLYURETHANES, Technomic Publishing, (1995) and include both aromatic and aliphatic diisocyanates. Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6hexamethylene diisocyanate (HDI), trimethylhexamethylene diisocyanate (TMDI), trans1,4-cyclohexane diisocyanate (CHDI), 1,4-cyclohexane bis(methylene isocyanate) (BDI), 1,3-cyclohexane bis(methylene isocyanate) ($H_6$XDI), isophorone diisocyanate (IPDI) and 4,4'-methylenebis(cyclohexyl isocyanate) ($H_2$ MDI). In some embodiments, the diisocyanate is isophorone diisocyanate, 1,6-hexamethylene diisocyanate, or 4,4'methylenebis (cyclohexyl isocyanate). A number of these diisocyanates are available from commercial sources such as Aldrich Chemical Company (Milwaukee, Wis., USA) or can be readily prepared by standard synthetic methods using literature procedures.

The quantity of diisocyanate used in the reaction mixture for the polyurethane/polyurea polymer compositions is typically about 50 mol % relative to the combination of the remaining reactants. More particularly, the quantity of diisocyanate employed in the preparation of the polyurethane/polyurea polymer will be sufficient to provide at least about 100% of the —NCO groups necessary to react with the hydroxyl or amino groups of the remaining reactants. For example, a polymer which is prepared using x moles of diisocyanate, will use a moles of a hydrophilic polymer (diol, diamine or combination), b moles of a silicone polymer having functionalized termini, and c moles of a chain extender, such that x=a+b+c, with the understanding that c can be zero.

Figure 4:
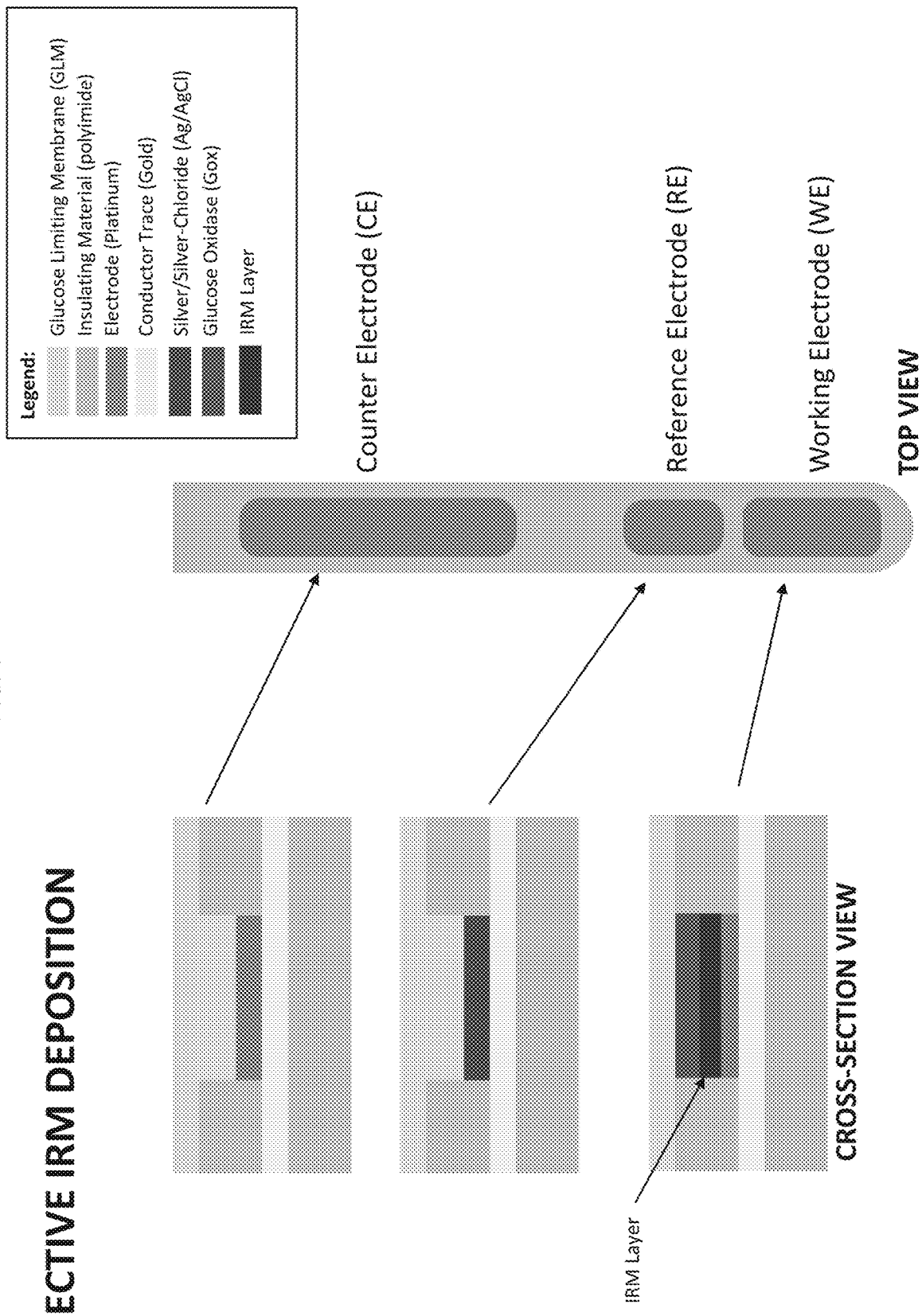
FIG. 4 provides schematics of a sensor embodiment showing selective deposition of an interference rejection membrane (IRM). The right panel shows cross-sectional views of materials deposited on a counter, reference and working electrode of a sensor that comprises a longitudinal base member as shown in the left panel (e.g. a longitudinal base member formed from a flexible polymeric material such as a polyimide, termed herein a "sensor flex element").
Figure 6:
FIG. 6 provides a flow chart (left panel) and a schematic cross section (right panel) of an embodiment of one method for making interference rejection membrane (IRM). This methodological embodiment of a deposition process involves a blended IRM reaction mixture that comprises glucose oxidase, GOx. Such embodiments of the invention aid adhesion of the sensor layers. Illustrative components of one embodiment of an IRM useful in such embodiments of the invention are included at the bottom of the figure.
Figure 7A:
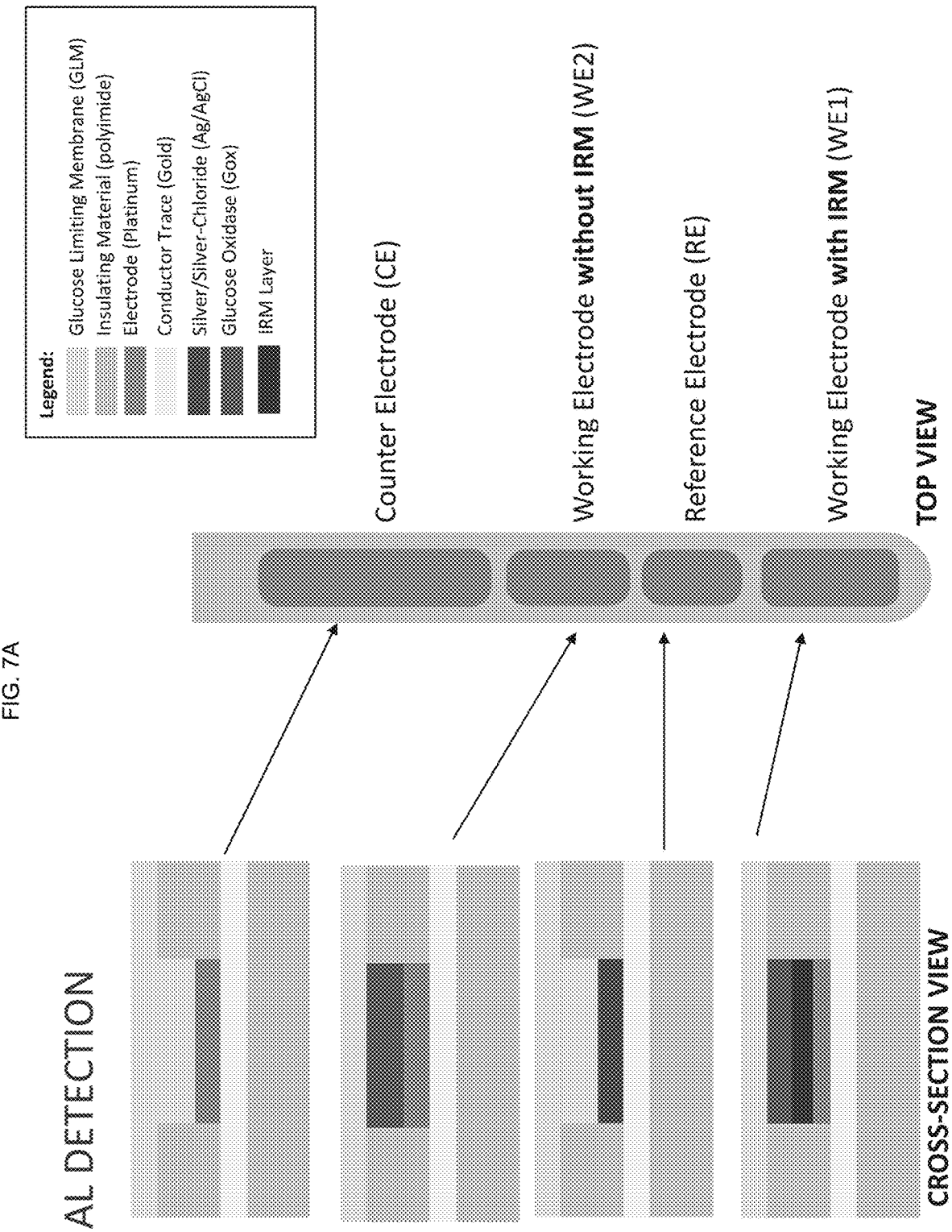
FIGS. 7A and 7B provide schematics of a sensor embodiment having two working electrodes, one of which is coated with an IRM and one of which is not. The right panel in FIG. 7A shows cross-sectional views of materials deposited on a counter, reference and two working electrodes of a sensor disposed on a longitudinal member as shown in the left panel (e.g. a sensor flex element).
Figure 7B:
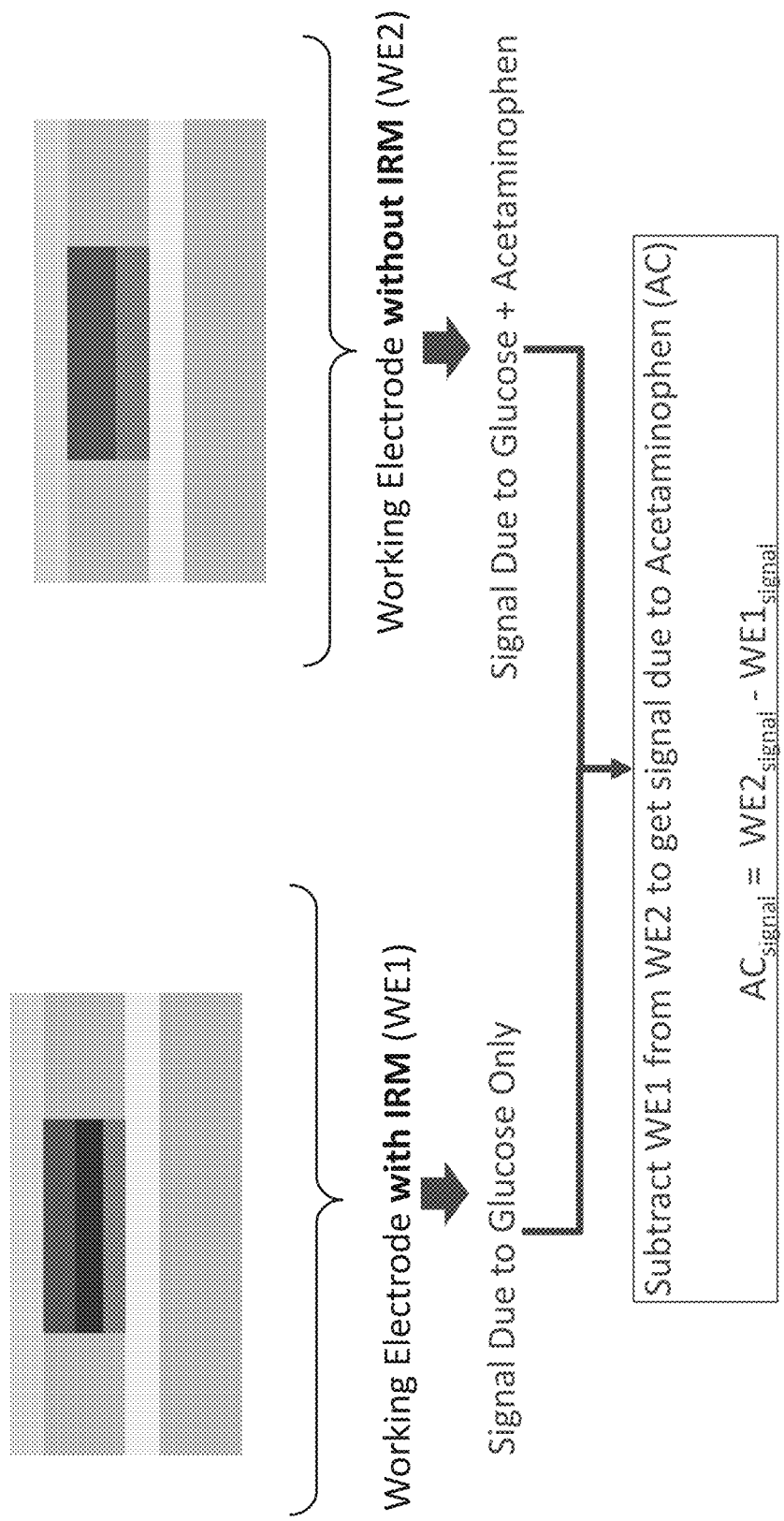

Another reactant used in the preparation of the polyurethane/polyurea polymers described herein is a hydrophilic polymer. The hydrophilic polymer can be a hydrophilic diol, a hydrophilic diamine or a combination thereof. The hydrophilic diol can be a poly(alkylene)glycol, a polyester-based polyol, or a polycarbonate polyol. As used herein, the term "poly(alkylene)glycol" refers to polymers of lower alkylene glycols such as poly(ethylene)glycol, poly(propylene)glycol and polytetramethylene ether glycol (PTMEG). The term "polyester-based polyol" refers to a polymer in which the R group is a lower alkylene group such as ethylene, 1,3-propylene, 1,2-propylene, 1,4-butylene,2,2-dimethyl-1,3-propylene, and the like (e.g. as depicted in FIG. 4 of U.S. Pat. No. 5,777,060). One of skill in the art will also understand that the diester portion of the polymer can also vary from the six-carbon diacid shown. For example, while FIG. 4 of U.S. Pat. No. 5,777,060 illustrates an adipic acid component, the present invention also contemplates the use of succinic acid esters, glutaric acid esters and the like. The term "polycarbonate polyol" refers those polymers having hydroxyl functionality at the chain termini and ether and carbonate functionality within the polymer chain. The alkyl portion of the polymer will typically be composed of C2 to C4 aliphatic radicals, or in some embodiments, longer chain aliphatic radicals, cycloaliphatic radicals or aromatic radicals. The term "hydrophilic diamines" refers to any of the above hydrophilic diols in which the terminal hydroxyl groups have been replaced by reactive amine groups or in which the terminal hydroxyl groups have been derivatized to produce an extended chain having terminal amine groups. For example, some hydrophilic diamines are a "diamino poly(oxyalkylene)" which is poly(alkylene)glycol in which the terminal hydroxyl groups are replaced with amino groups. The term "diamino poly(oxyalkylene" also refers to poly(alkylene)glycols which have aminoalkyl ether groups at the chain termini. One example of a suitable diamino poly(oxyalkylene) is poly(propylene glycol)bis(2-aminopropyl ether). A number of the above polymers can be obtained from Aldrich Chemical Company. Alternatively, conventional methods known in the art can be employed for their synthesis.

Silicone containing polyurethane/polyurea polymers which are useful in the present invention are typically linear, have excellent oxygen permeability and essentially no glucose permeability. Typically, the silicone polymer is a polydimethylsiloxane having two reactive functional groups (i.e., a functionality of 2). The functional groups can be, for example, hydroxyl groups, amino groups or carboxylic acid groups, but are typically hydroxyl or amino groups. In some embodiments, combinations of silicone polymers can be used in which a first portion comprises hydroxyl groups and a second portion comprises amino groups. Typically, the functional groups are positioned at the chain termini of the silicone polymer. A number of suitable silicone polymers are commercially available from such sources as Dow Chemical Company (Midland, Mich., USA) and General Electric Company (Silicones Division, Schenectady, N.Y., USA).

Still others can be prepared by general synthetic methods known in the art (see, e.g. U.S. Pat. No. 5,777,060), beginning with commercially available siloxanes (United Chemical Technologies, Bristol. Pa., USA). For use in the present invention, the silicone polymers will typically be those having a molecular weight of from about 400 to about 10,000, more typically those having a molecular weight of from about 2000 to about 4000. The amount of silicone polymer which is incorporated into the reaction mixture will depend on the desired characteristics of the resulting polymer from which the biocompatible membrane is formed. For those compositions in which a lower glucose penetration is desired, a larger amount of silicone polymer can be employed. Alternatively, for compositions in which a higher glucose penetration is desired, smaller amounts of silicone polymer can be employed. Typically, for a glucose sensor, the amount of siloxane polymer will be from 10% to 90% by mole relative to the diisocyanate. Typically, the amount is from about 20% to 60% by mole relative to the diisocyanate.

In one group of embodiments, the reaction mixture for the preparation of biocompatible membranes will also contain a chain extender which is an aliphatic or aromatic diol, an aliphatic or aromatic diamine, alkanolamine, or combinations thereof (e.g. as depicted in FIG. 8 of U.S. Pat. No. 5,777,060)). Examples of suitable aliphatic chain extenders include ethylene glycol, propylene glycol, 1,4-butanediol, 1,6-hexanediol, ethanolamine, ethylene diamine, butane diamine, 1,4-cyclohexanedimethanol. Aromatic chain extenders include, for example, para-di(2-hydroxyethoxy) benzene, meta-di(2-hydroxyethoxy)benzene, Ethacure 100® (a mixture of two isomers of 2,4-diamino-3,5-diethyltoluene), Ethacure 300® (2,4-diamino-3,5-di(methylthio) toluene), 3,3'-dichloro-4,4'diaminodiphenylmethane, Polacure® 740M (trimethylene glycol bis(para-aminobenzoate) ester), and methylenedianiline. Incorporation of one or more of the above chain extenders typically provides the resulting biocompatible membrane with additional physical strength, but does not substantially increase the glucose permeability of the polymer. Typically, a chain extender is used when lower (i.e., 10-40 mol %) amounts of hydrophilic polymers are used. In particularly some compositions, the chain extender is diethylene glycol which is present in from about 40% to 60% by mole relative to the diisocyanate.

Polymerization of the above reactants can be carried out in bulk or in a solvent system. Use of a catalyst is some, though not required. Suitable catalysts include dibutyltin bis(2-ethylhexanoate) (CAS #: 2781-10-4), dibutyltin diacetate, triethylamine and combinations thereof. Typically dibutyltin bis(2-ethylhexanoate is used as the catalyst. The typical amount of this catalyst used is in the formulation is from 0.05% to 0.2% (w/w ratio). Bulk polymerization is typically carried out at an initial temperature of about 25° C. (ambient temperature) to about 50° C., in order to insure adequate mixing of the reactants. Upon mixing of the reactants, an exotherm is typically observed, with the temperature rising to about 90-120° C. After the initial exotherm, the reaction flask can be heated at from 75° C. to 125° C., with 90°. C. to 100° C. being an exemplary temperature range. Heating is usually carried out for one to two hours. Solution polymerization can be carried out in a similar manner. Solvents which are suitable for solution polymerization include dimethylformamide, dimethyl sulfoxide, dimethylacetamide, halogenated solvents such as 1,2,3-trichloropropane, and ketones such as 4-methyl-2-pentanone. Typically, THF is used as the solvent. When polymerization is carried out in a solvent, heating of the reaction mixture is typically carried out for three to four hours.

Polymers prepared by bulk polymerization are typically dissolved in dimethylformamide and precipitated from water. Polymers prepared in solvents that are not miscible with water can be isolated by vacuum stripping of the solvent. These polymers are then dissolved in dimethylformamide and precipitated from water. After thoroughly washing with water, the polymers can be dried in vacuo at about 50° C. to constant weight.

Preparation of the membranes can be completed by dissolving the dried polymer in a suitable solvent and cast a film onto a glass plate. The selection of a suitable solvent for casting will typically depend on the particular polymer as well as the volatility of the solvent. Typically, the solvent is THF, $CHCl_3$, $CH_2Cl_2$, DMF, IPA or combinations thereof. More typically, the solvent is THF or DMF/$CH_2Cl_2$ (2/98 volume %). The solvent is removed from the films, the resulting membranes are hydrated fully, their thicknesses measured and water pickup is determined. Membranes which are useful in the present invention will typically have a water pickup of about 20 to about 100%, typically 30 to about 90%, and more typically 40 to about 80%, by weight.

Oxygen and glucose diffusion coefficients can also be determined for the individual polymer compositions. Methods for determining diffusion coefficients are known to those of skill in the art, and examples are provided below. Certain embodiments of the biocompatible membranes described herein will typically have an oxygen diffusion coefficient ($D_{oxygen}$) of about $0.1 \times 10^{-6}$ $cm^2/sec$ to about $2.0 \times 10^{-6}$ $cm^2/sec$ and a glucose diffusion coefficient ($D_{glucose}$) of about $1 \times 10^{-9}$ $cm^2/sec$ to about $500 \times 10^{-9}$ $cm^2/sec$. More typically, the glucose diffusion coefficient is about $10 \times 10^{-9}$ $cm^2/sec$ to about $200 \times 10^{-9}$ $cm^2/sec$.

Diagrammatic Illustration of Typical Sensor Configurations

Figure 2B:
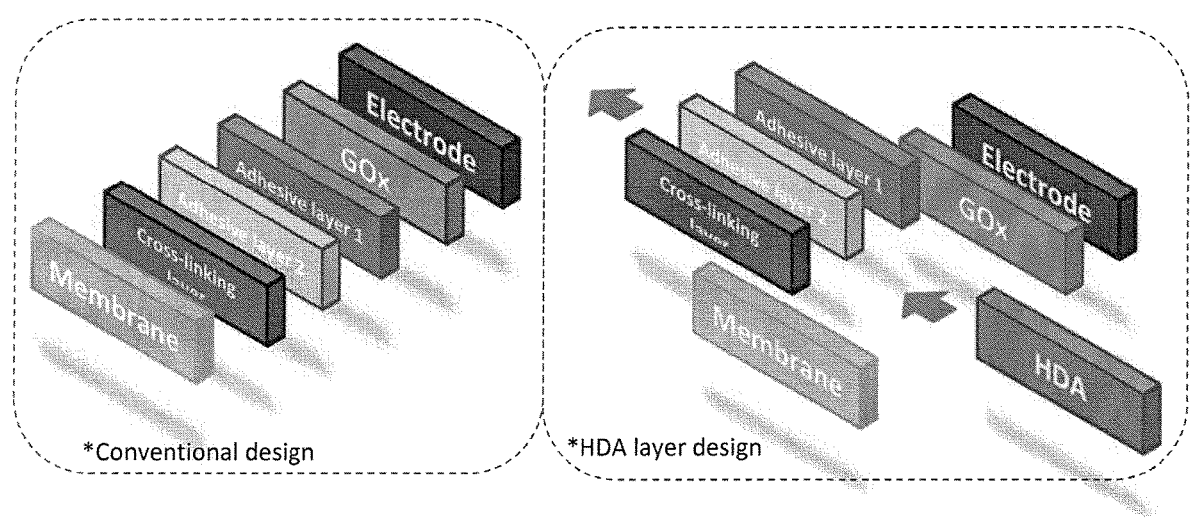
Figure 3:
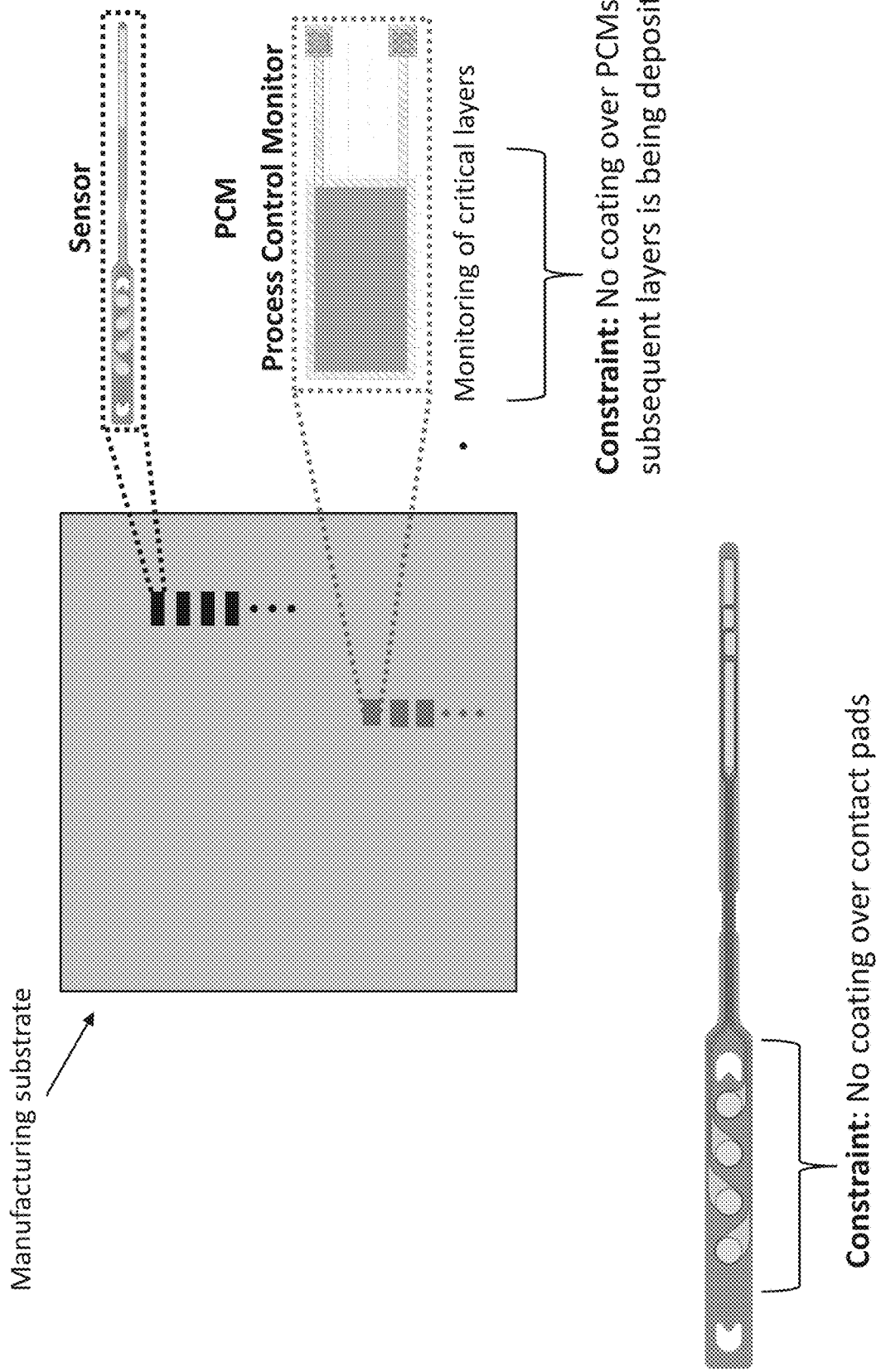
FIG. 3 provides a schematic showing manufacturing and analyte sensor elements of the invention. The central rectangular element illustrates a sensor manufacturing plate, with the drawings to the right of this sensor manufacturing plate show a sensor embodiment comprising electrodes disposed on a thin flexible base substrate (upper right) and a process control monitor (lower right) and well as a drawing below this photograph showing a sensor embodiment and the constraints associated with no coatings over the contact pads of the sensor. This figure is used to illustrate that while an Interference Rejection Membrane (IRM) is useful to block Acetaminophen and other drugs that can cause spurious signals at amperometric analyte sensors (e.g. for better closed loop control in glucose sensors), during sensor manufacture, such IRMs cannot be blanket coated over an entire wafer due to possibility of undesirable coverage of Process Control Monitors (PCMs) & Contact pads with the IRM.

FIG. 2A illustrates a cross-section of a conventional sensor embodiment 100. The components of the sensor are typically characterized herein as layers in this layered electrochemical sensor stack because, for example, it allows for a facile characterization of conventional sensor structures such as those shown in FIG. 2A and their differences from the invention disclosed herein as shown in FIG. 2B (i.e. ones comprising a high density amine (HAD) layer comprising poly-1-lysine polymers having molecular weights between 30 KDa and 300 KDa). Artisans will understand, that in certain embodiments of the invention, the sensor constituents are combined such that multiple constituents form one or more heterogeneous layers. In this context, those of skill in the art understand that, while certain layers/components of conventional sensor embodiments are useful in the HDA sensors disclosed herein, the placement and composition of the layered constituents is very different in HDA sensor embodiments of the invention. Those of skill in this art will understand that certain embodiments if the invention include elements/layers that are found in conventional sensors while others are excluded, and/or new material layers/elements are included. For example, certain elements disclosed in FIG. 2A are also found in the invention disclosed herein (e.g. a base, analyte sensing layer, an analyte modulating layer etc.) while, as shown in FIG. 2B, other elements are not (e.g. separate HSA protein layers, layers comprising a siloxane adhesion promoter etc.). Similarly, embodiments of the invention include layers/elements having materials disposed in unique configurations that are not found in conventional sensors (e.g. high-density amine (HDA) polymer layers).

The embodiment shown in FIG. 2A includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102. Typically the conductive layer 104 comprises one or more electrodes. An operating sensor 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating can be disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2A, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. In the sensor configuration shown in FIG. 2B, an interference rejection membrane 120 is disposed on one or more of the exposed electrodes of the conductive layer 104, with the analyte sensing layer 110 then being disposed on this interference rejection membrane 120. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

In embodiments of the invention, the analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns (μm) in thickness, typically the analyte sensing layer or sublayer is relatively thin as compared to those found in sensors previously described in the art, and is for example, typically less than 1, 0.5, 0.25 or 0.1 microns in thickness. As discussed in detail below, some methods for generating a thin analyte sensing layer 110 include brushing the layer onto a substrate (e.g. the reactive surface of a platinum black electrode), as well as spin coating processes, dip and dry processes, low shear spraying processes, ink-jet printing processes, silk screen processes and the like.

Typically, the analyte sensing layer 110 is coated and or disposed next to one or more additional layers. Optionally, the one or more additional layers includes a protein layer 116 disposed upon the analyte sensing layer 110. Typically, the protein layer 116 comprises a protein such as human serum albumin, bovine serum albumin or the like. Typically, the protein layer 116 comprises human serum albumin. In some embodiments of the invention, an additional layer includes an analyte modulating layer 112 that is disposed above the analyte sensing layer 110 to regulate analyte access with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, NAFION, polyester sulfonic acids (e.g. Kodak AQ), hydrogels, the polymer blends disclosed herein or any other suitable hydrophilic membranes known to those skilled in the art.

In some embodiments of the invention, an adhesion promoter layer 114 is disposed between layers such as the analyte modulating layer 112 and the analyte sensing layer 110 as shown in FIG. 2A in order to facilitate their contact and/or adhesion. In a specific embodiment of the invention, an adhesion promoter layer 114 is disposed between the analyte modulating layer 112 and the protein layer 116 as shown in FIG. 2A in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

Embodiments of typical elements used to make the sensors disclosed herein are discussed below.

Typical Analyte Sensor Constituents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g. element 102 in FIG. 2A). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

The base constituent may be self-supporting or further supported by another material as is known in the art. In one embodiment of the sensor configuration shown in FIG. 2A, the base constituent 102 comprises a ceramic. Alternatively, the base constituent comprises a polymeric material such as a polyimide. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 50, 100, 200, 300, 400, 500 or 1000 microns). Alternatively, one can utilize a nonconductive ceramic, such as alumina, in thin constituents, e.g., less than about 30 microns.

Conductive Constituent

The electrochemical sensors of the invention typically include a conductive constituent disposed upon the base constituent that includes at least one electrode for measuring an analyte or its byproduct (e.g. oxygen and/or hydrogen peroxide) to be assayed (see, e.g. element 104 in FIG. 2A). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively, the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate.

Typically for in vivo use, embodiments of the present invention are implanted subcutaneously in the skin of a mammal for direct contact with the body fluids of the mammal, such as blood. Alternatively, the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal. Embodiments of the invention include sensors comprising electrodes constructed from nanostructured materials. As used herein, a "nanostructured material" is an object manufactured to have at least one dimension smaller than 100 nm. Examples include, but are not limited to, single-walled nanotubes, double-walled nanotubes, multi-walled nanotubes, bundles of nanotubes, fullerenes, cocoons, nanowires, nanofibres, onions and the like.

Interference Rejection Constituent

The electrochemical sensors of the invention include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. The interference rejection layer is typically formed by a reaction mixture comprising a polymerizable acrylate monomer, a crosslinking agent and a photoinitiator agent; and the interference rejection layer is cured when the reaction mixture is polymerized by exposure to light, either in single curing steps or curing steps comprising multiple exposures to light. Typically, the acrylate monomer comprises a hydroxyethylmethacrylate monomer, a methyl methacrylate monomer and/or a hydroxybutyl methacrylate monomer; and the crosslinking agent comprises an ethylene glycol and/or a silane. The photoinitiator agent used in such reaction mixtures is typically a diazo photoactive compound Certain interference rejection constituents' function via size exclusion (e.g. by excluding interfering species of a specific size). Examples of interference rejection constituents include one or more layers or coatings of compounds such as hydrophilic crosslinked pHEMA and polylysine polymers as well as cellulose acetate (including cellulose acetate incorporating agents such as poly(ethylene glycol)), polyethersulfones, polytetra-fluoroethylenes, the perfluorinated ionomer NAFION, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference. Other interference rejection constituents include for example those observed to limit the movement of compounds based upon a molecular weight range, for example cellulose acetate as disclosed for example in U.S. Pat. No. 5,755,939, the contents of which are incorporated by reference. Additional compositions having an unexpected constellation of material properties that make them ideal for use as interference rejection membranes in certain amperometric glucose sensors as well as methods for making and using them are disclosed herein, for example in U.S. patent application Ser. No. 12/572,087.

Analyte Sensing Constituent

The electrochemical sensors of the invention include an analyte sensing constituent disposed on the electrodes of the sensor (see, e.g. element 110 in FIG. 2A). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide, wherein the hydrogen peroxide so generated is anodically detected at the working electrode in the conductive constituent.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture.

Protein Constituent

The electrochemical sensors of the invention optionally include a protein constituent disposed between the analyte sensing constituent and the analyte modulating constituent (see, e.g. element 116 in FIG. 2A). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2A). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula R'Si(OR)$_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase (GOx) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such a the analyte sensing constituent and/or the protein constituent and or a siloxane moiety present in a compound disposed in a proximal layer such as the analyte modulating layer.

Analyte Modulating Constituent

The electrochemical sensors of the invention include an analyte modulating constituent disposed on the sensor (see, e.g. element 112 in FIG. 2A). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane (e.g. a glucose limiting membrane) which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferents, such as ascorbic acid and uric acid, diffuse through a primary membrane of the sensor. As the glucose, oxygen and interferents reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868 and 5,391,250, the disclosures of each being incorporated herein by reference. The hydrogels described therein are particularly useful with a variety of implantable devices for which it is advantageous to provide a surrounding water constituent.

Cover Constituent

The electrochemical sensors of the invention include one or more cover constituents which are typically electrically insulating protective constituents (see, e.g. element 106 in FIG. 2A). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Illustrative Embodiments of Analyte Sensor Apparatus and Associated Characteristics The analyte sensor apparatus disclosed herein has a number of embodiments. A general embodiment of the invention is an analyte sensor apparatus for implantation within a mammal. While the analyte sensors are typically designed to be implantable within the body of a mammal, the sensors are not limited to any particular environment and can instead be used in a wide variety of contexts, for example for the analysis of most liquid samples including biological fluids such as whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

As noted above, the sensor embodiments disclosed herein can be used to sense analytes of interest in one or more physiological environments. In certain embodiments for example, the sensor can be in direct contact with interstitial fluids as typically occurs with subcutaneous sensors. The sensors of the present invention may also be part of a skin surface system where interstitial glucose is extracted through the skin and brought into contact with the sensor (see, e.g. U.S. Pat. Nos. 6,155,992 and 6,706,159 which are incorporated herein by reference). In other embodiments, the sensor can be in contact with blood as typically occurs for example with intravenous sensors. The sensor embodiments of the invention further include those adapted for use in a variety of contexts. In certain embodiments for example, the sensor can be designed for use in mobile contexts, such as those employed by ambulatory users. Alternatively, the sensor can be designed for use in stationary contexts such as those adapted for use in clinical settings. Such sensor embodiments include, for example, those used to monitor one or more analytes present in one or more physiological environments in a hospitalized patient.

Sensors of the invention can also be incorporated into a wide variety of medical systems known in the art. Sensors of the invention can be used, for example, in a closed loop infusion system designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Permutations of Analyte Sensor Apparatus and Elements

As noted above, the invention disclosed herein includes a number of embodiments including sensors having constellations of elements including polymeric compositions. Such embodiments of the invention allow artisans to generate a variety of permutations of the analyte sensor apparatus disclosed herein. As noted above, illustrative general embodiments of the sensor disclosed herein include a base layer, a cover layer and at least one layer having a sensor element such as an electrode disposed between the base and cover layers. Typically, an exposed portion of one or more sensor elements (e.g., a working electrode, a counter electrode, reference electrode, etc.) is coated with a very thin layer of material having an appropriate electrode chemistry. For example, an enzyme such as lactate oxidase, glucose oxidase, glucose dehydrogenase or hexokinase, can be disposed on the exposed portion of the sensor element within an opening or aperture defined in the cover layer. FIG. 2A illustrates a cross-section of a typical sensor structure 100 of the present invention. The sensor is formed from a plurality of layers of various conductive and non-conductive constituents disposed on each other according to a method of the invention to produce a sensor structure 100.

As noted above, in the sensors of the invention, the various layers (e.g. the analyte sensing layer) of the sensors can have one or more bioactive and/or inert materials incorporated therein. The term "incorporated" as used herein is meant to describe any state or condition by which the material incorporated is held on the outer surface of or within a solid phase or supporting matrix of the layer. Thus, the material "incorporated" may, for example, be immobilized, physically entrapped, attached covalently to functional groups of the matrix layer(s). Furthermore, any process, reagents, additives, or molecular linker agents which promote the "incorporation" of said material may be employed if these additional steps or agents are not detrimental to, but are consistent with the objectives of the present invention. This definition applies, of course, to any of the embodiments of the present invention in which a bioactive molecule (e.g. an enzyme such as glucose oxidase) is "incorporated." For example, certain layers of the sensors disclosed herein include a proteinaceous substance such as albumin which serves as a crosslinkable matrix. As used herein, a proteinaceous substance is meant to encompass substances which are generally derived from proteins whether the actual substance is a native protein, an inactivated protein, a denatured protein, a hydrolyzed species, or a derivatized product thereof. Examples of suitable proteinaceous materials include, but are not limited to enzymes such as glucose oxidase and lactate oxidase and the like, albumins (e.g. human serum albumin, bovine serum albumin etc.), caseins, gamma-globulins, collagens and collagen derived products (e.g., fish gelatin, fish glue, animal gelatin, and animal glue).

An illustrative embodiment of the invention is shown in FIG. 2A. This embodiment includes an electrically insulating base layer 102 to support the sensor 100. The electrically insulating layer base 102 can be made of a material such as a ceramic substrate, which may be self-supporting or further supported by another material as is known in the art. In an alternative embodiment, the electrically insulating layer 102 comprises a polyimide substrate, for example a polyimide tape, dispensed from a reel. Providing the layer 102 in this form can facilitate clean, high density mass production. Further, in some production processes using such a polyimide tape, sensors 100 can be produced on both sides of the tape.

Typical embodiments of the invention include an analyte sensing layer disposed on the base layer 102. In an illustrative embodiment as shown in FIG. 2A the analyte sensing layer comprises a conductive layer 104 which is disposed on insulating base layer 102. Typically the conductive layer 104 comprises one or more electrodes. The conductive layer 104 can be applied using many known techniques and materials as will be described hereafter, however, the electrical circuit of the sensor 100 is typically defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating protective cover layer 106 such as a polymer coating is typically disposed on portions of the conductive layer 104. Acceptable polymer coatings for use as the insulating protective layer 106 can include, but are not limited to, non-toxic biocompatible polymers such as polyimide, biocompatible solder masks, epoxy acrylate copolymers, or the like. Further, these coatings can be photo-imageable to facilitate photolithographic forming of apertures 108 through to the conductive layer 104. In certain embodiments of the invention, an analyte sensing layer is disposed upon a porous metallic and/or ceramic and/or polymeric matrix with this combination of elements functioning as an electrode in the sensor.

In the sensors of the present invention, one or more exposed regions or apertures 108 can be made through the protective layer 106 to the conductive layer 104 to define the contact pads and electrodes of the sensor 100. In addition to photolithographic development, the apertures 108 can be formed by a number of techniques, including laser ablation, chemical milling or etching or the like. A secondary photoresist can also be applied to the cover layer 106 to define the regions of the protective layer to be removed to form the apertures 108. An operating sensor 100 typically includes a plurality of electrodes such as a working electrode and a counter electrode electrically isolated from each other, however typically situated in close proximity to one another. Other embodiments may also include a reference electrode. Still other embodiments may utilize a separate reference element not formed on the sensor. The exposed electrodes and/or contact pads can also undergo secondary processing through the apertures 108, such as additional plating processing, to prepare the surfaces and/or strengthen the conductive regions.

An analyte sensing layer 110 is typically disposed on one or more of the exposed electrodes of the conductive layer 104 through the apertures 108. Typically, the analyte sensing layer 110 is a sensor chemistry layer and most typically an enzyme layer. Typically, the analyte sensing layer 110 comprises the enzyme glucose oxidase or the enzyme lactate oxidase. In such embodiments, the analyte sensing layer 110 reacts with glucose to produce hydrogen peroxide which modulates a current to the electrode which can be monitored to measure an amount of glucose present. The sensor chemistry layer 110 can be applied over portions of the conductive layer or over the entire region of the conductive layer. Typically the sensor chemistry layer 110 is disposed on portions of a working electrode and a counter electrode that comprise a conductive layer. Some methods for generating the thin sensor chemistry layer 110 include spin coating processes, dip and dry processes, low shear spraying processes, ink-jet printing processes, silk screen processes and the like. Most typically the thin sensor chemistry layer 110 is applied using a spin coating process.

The analyte sensing layer 110 is typically coated with one or more coating layers. In some embodiments of the invention, one such coating layer includes a membrane which can regulate the amount of analyte that can contact an enzyme of the analyte sensing layer. For example, a coating layer can comprise an analyte modulating membrane layer such as a glucose limiting membrane which regulates the amount of glucose that contacts the glucose oxidase enzyme layer on an electrode. Such glucose limiting membranes can be made from a wide variety of materials known to be suitable for such purposes, e.g., silicone, polyurethane, polyurea cellulose acetate, Nafion, polyester sulfonic acid (Kodak AQ), hydrogels or any other membrane known to those skilled in the art. In certain embodiments of the invention, the analyte modulating layer comprises a linear polyurethane/polyurea polymer polycarbonate with a branched acrylate hydrophilic comb-copolymer having a central chain and a plurality of side chains coupled to the central chain, wherein at least one side chain comprises a silicone moiety.

In some embodiments of the invention, a coating layer is a glucose limiting membrane layer 112 which is disposed above the sensor chemistry layer 110 to regulate glucose contact with the sensor chemistry layer 110. In some embodiments of the invention, an adhesion promoter layer 114 is disposed between the membrane layer 112 and the sensor chemistry layer 110 as shown in FIG. 2A in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the sensor chemistry layer 110 can be sufficiently crosslinked or otherwise prepared to allow the membrane layer 112 to be disposed in direct contact with the sensor chemistry layer 110 in the absence of an adhesion promoter layer 114.

As noted above, embodiments of the present invention can include one or more functional coating layers. As used herein, the term "functional coating layer" denotes a layer that coats at least a portion of at least one surface of a sensor, more typically substantially all of a surface of the sensor, and that is capable of interacting with one or more analytes, such as chemical compounds, cells and fragments thereof, etc., in the environment in which the sensor is disposed. Non-limiting examples of functional coating layers include sensor chemistry layers (e.g., enzyme layers), analyte limiting layers, biocompatible layers; layers that increase the slipperiness of the sensor; layers that promote cellular attachment to the sensor; layers that reduce cellular attachment to the sensor; and the like. Typically analyte modulating layers operate to prevent or restrict the diffusion of one or more analytes, such as glucose, through the layers. Optionally such layers can be formed to prevent or restrict the diffusion of one type of molecule through the layer (e.g. glucose), while at the same time allowing or even facilitating the diffusion of other types of molecules through the layer (e.g. $O_2$). An illustrative functional coating layer is a hydrogel such as those disclosed in U.S. Pat. Nos. 5,786,439 and 5,391,250, the disclosures of each being incorporated herein by reference. The hydrogels described therein are particularly useful with a variety of implantable devices for which it is advantageous to provide a surrounding water layer.

The sensor embodiments disclosed herein can include layers having UV-absorbing polymers. In accordance with one aspect of the present invention, there is provided a sensor including at least one functional coating layer including an UV-absorbing polymer. In some embodiments, the UV-absorbing polymer is a polyurethane, a polyurea or a polyurethane/polyurea copolymer. More typically, the selected UV-absorbing polymer is formed from a reaction mixture including a diisocyanate, at least one diol, diamine or mixture thereof, and a polyfunctional UV-absorbing monomer.

UV-absorbing polymers are used with advantage in a variety of sensor fabrication methods, such as those described in U.S. Pat. No. 5,390,671, to Lord et al., entitled "Transcutaneous Sensor Insertion Set"; U.S. Pat. No. 5,165,407, to Wilson et al., entitled "Implantable Glucose Sensor"; and U.S. Pat. No. 4,890,620, to Gough, entitled "Two-Dimensional Diffusion Glucose Substrate Sensing Electrode", which are incorporated herein in their entireties by reference. However, any sensor production method which includes the step of forming an UV-absorbing polymer layer above or below a sensor element is considered to be within the scope of the present invention. In particular, the inventive methods are not limited to thin-film fabrication methods, and can work with other sensor fabrication methods that utilize UV-laser cutting. Embodiments can work with thick-film, planar or cylindrical sensors and the like, and other sensor shapes requiring laser cutting.

As disclosed herein, the sensors of the present invention are particularly designed for use as subcutaneous or transcutaneous glucose sensors for monitoring blood glucose levels in a diabetic patient. Typically each sensor comprises a plurality of sensor elements, for example electrically conductive elements such as elongated thin film conductors, formed between an underlying insulative thin film base layer and an overlying insulative thin film cover layer.

If desired, a plurality of different sensor elements can be included in a single sensor. For example, both conductive and reactive sensor elements can be combined in one sensor, optionally with each sensor element being disposed on a different portion of the base layer. One or more control elements can also be provided. In such embodiments, the sensor can have defined in its cover layer a plurality of openings or apertures. One or more openings can also be defined in the cover layer directly over a portion of the base layer, in order to provide for interaction of the base layer with one or more analytes in the environment in which the sensor is disposed. The base and cover layers can be comprised of a variety of materials, typically polymers. In more specific embodiments the base and cover layers are comprised of an insulative material such as a polyimide. Openings are typically formed in the cover layer to expose distal end electrodes and proximal end contact pads. In a glucose monitoring application, for example, the sensor can be placed transcutaneously so that the distal end electrodes are in contact with patient blood or extracellular fluid, and the contact pads are disposed externally for convenient connection to a monitoring device.

Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al., "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A typical embodiment of the invention disclosed herein is a method of making a sensor apparatus for implantation within a mammal comprising the steps of: providing a base layer; forming a conductive layer on the base layer, wherein the conductive layer includes an electrode (and typically a working electrode, a reference electrode and a counter electrode); forming an analyte sensing layer on the conductive layer, wherein the analyte sensing layer includes a composition that can alter the electrical current at the electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In certain embodiments of the invention, the analyte modulating layer comprises a linear polyurethane/polyurea polymer polycarbonate with a branched acrylate copolymer having a central chain and a plurality of side chains coupled to the central chain. In some embodiments of these methods, the analyte sensor apparatus is formed in a planar geometric configuration As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, N.Y. (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

As noted above, appropriate electrode chemistries defining the distal end electrodes can be applied to the sensor tips, optionally subsequent to exposure of the sensor tips through the openings. In an illustrative sensor embodiment having three electrodes for use as a glucose sensor, an enzyme (typically glucose oxidase) is provided within one of the openings, thus coating one of the sensor tips to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor.

Methods for producing the extremely thin enzyme coatings of the invention include spin coating processes, dip and dry processes, low shear spraying processes, ink-jet printing processes, silk screen processes and the like. As artisans can readily determine the thickness of an enzyme coat applied by process of the art, they can readily identify those methods capable of generating the extremely thin coatings of the invention. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes. Consequently, yet another embodiment of the invention is a method of avoiding the electrodeposition influenced cracking and/or delamination of a coating on a sensor comprising applying the coating via a spin coating process.

Methods for Using Analyte Sensor Apparatus of the Invention

A related embodiment of the invention is a method of sensing an analyte within the body of a mammal, the method comprising implanting an analyte sensor embodiment disclosed herein in to the mammal and then sensing an alteration in current at the working electrode and correlating the alteration in current with the presence of the analyte, so that the analyte is sensed. The analyte sensor can polarized anodically such that the working electrode where the alteration in current is sensed is an anode, or cathodically such that the working electrode where the alteration in current is sensed is a cathode. In one such method, the analyte sensor apparatus senses glucose in the mammal. In an alternative method, the analyte sensor apparatus senses lactate, potassium, calcium, oxygen, pH, and/or any physiologically relevant analyte in the mammal.

Certain analyte sensors having the IRM and/or analyte modulating compositions the structures discussed above have a number of highly desirable characteristics which allow for a variety of methods for sensing analytes in a mammal. For example, in such methods, the analyte sensor apparatus implanted in the mammal functions to sense an analyte within the body of a mammal for more than 1, 2, 3, 4, 5, or 6 weeks. Typically, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example interstitially, as well as in both vascular and other non-vascular spaces.

The invention claimed is:

1. A method of making an amperometric analyte sensor for implantation within a mammal comprising the steps of:
   providing a first base layer;
   forming a conductive layer on the first base layer, wherein the conductive layer includes a first working electrode;
   forming an analyte sensing layer on the conductive layer, wherein the analyte sensing layer includes an enzyme selected to generate a detectable electrical signal upon exposure to an analyte, wherein:

the analyte sensing layer is formed by combining a polymerizable monomer, a crosslinking agent and a photoinitiator agent;

forming an interference rejection layer on the analyte sensing layer, wherein:

the interference rejection layer is formed by a reaction mixture comprising a polymerizable monomer, a crosslinking agent and a photoinitiator agent;

the reaction mixture comprises a 15% to 96% of crosslinker to monomer ratio; and the analyte sensing layer and the interference rejection layer are formed when the reaction mixture is polymerized by exposure to light; and forming an analyte modulating layer on the interference rejection layer; such that an amperometric analyte sensor for implantation within a mammal is made.

2. The method of claim 1, wherein:
(a) the reaction mixture forms a polyvinyl alcohol polymer or a poly(2-hydroxyethyl methacrylate) polymer;
(b) polymerizable monomer comprises a hydroxyethylmethacrylate monomer, a methyl methacrylate monomer and/or a hydroxybutyl methacrylate monomer;
(c) the crosslinking agent comprises an ethylene glycol and/or a silane; and/or
(d) relative amounts of crosslinking agent and polymerizable monomer disposed within the reaction mixture are selected such that the reaction mixture comprises 50%-80% crosslinking agent and 20%-50% polymerizable monomer.

3. The method of claim 2, wherein the analyte sensing layer is formed by combining a polymerizable monomer, a crosslinking agent and a photoinitiator agent and the analyte sensing layer is formed when the reaction mixture is polymerized by exposure to light.

4. The method of claim 1, wherein:
the reaction mixture comprises a diazo photoreactive crosslinking agent;
the reaction mixture comprises an ethylene glycol diacrylate crosslinking agent; and/or
the method of claim 1 further comprises forming a layer comprising an ascorbic acid oxidase enzyme.

5. The method of claim 4, wherein:
the layer comprising an ascorbic acid oxidase enzyme comprises glucose oxidase or comprises an analyte modulating layer; or
the layer comprising an ascorbic acid oxidase enzyme does not comprise glucose oxidase or does not comprise an analyte modulating layer.

6. The method of claim 1, wherein:
the conductive layer includes a second working electrode, wherein said second working electrode comprises an analyte sensing layer and an analyte modulating layer and does not comprise an interference rejection layer; and/or
the conductive layer includes a background electrode, wherein said background electrode does not comprise an analyte sensing layer, an analyte modulating layer; or an interference rejection layer.

7. The method of claim 1, wherein the interference rejection layer is formed in a single step comprising exposure to light.

8. The method of claim 1, wherein the interference rejection layer is formed in a plurality of steps comprising exposure to light.

9. The method of claim 8, wherein the plurality of steps comprising exposure to light comprises:
a first exposure to light selected to partially polymerize the interference rejection reaction mixture comprising a polymerizable monomer, a crosslinking agent and a photoinitiator agent; and
a second exposure to light selected to fully polymerize:
the reaction mixture comprising a polymerizable monomer, a crosslinking agent and a photoinitiator agent; and
the partially polymerized interference rejection reaction mixture.

10. The method of claim 7, wherein at least one interference rejection reaction mixture is selectively disposed on a location on the first base layer and/or one photomask is used to selectively polymerize an interference rejection reaction mixture disposed on the first base layer such that contact pads and/or conductor traces disposed on the first base layer do not comprise an interference rejection layer.

* * * * *